US011589895B1

(12) United States Patent
Rivera et al.

(10) Patent No.: US 11,589,895 B1
(45) Date of Patent: Feb. 28, 2023

(54) TISSUE SEPARATION DEVICE AND METHODS FOR USING SAME

(71) Applicant: Musculoskeletal Transplant Foundation, Edison, NJ (US)

(72) Inventors: German Eduardo Jurado Rivera, Rahway, NJ (US); Moises Rivera-Alvarado, Easton, PA (US); Samuel Arocho, Rockaway, NJ (US); Walter E. Diaz, Easton, PA (US); Manuel A. Olivos Sanchez, Belleville, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 233 days.

(21) Appl. No.: 16/996,362

(22) Filed: Aug. 18, 2020

Related U.S. Application Data

(60) Provisional application No. 62/888,831, filed on Aug. 19, 2019.

(51) Int. Cl.
*A61B 17/322* (2006.01)

(52) U.S. Cl.
CPC .... *A61B 17/322* (2013.01); *A61B 2017/3225* (2013.01)

(58) Field of Classification Search
CPC .......... A61B 17/322; A61B 2017/3225; A61B 17/32002; A61B 17/142
See application file for complete search history.

(56) References Cited

U.S. PATENT DOCUMENTS

| | | | |
|---|---|---|---|
| 2,590,299 A * | 3/1952 | Douglas | A61B 17/322 606/132 |
| 7,625,384 B2 | 12/2009 | Eriksson | |
| 10,537,349 B1 | 1/2020 | Hayzlett et al. | |
| 11,185,346 B1 | 11/2021 | Wu et al. | |
| 2011/0077664 A1 | 3/2011 | Schultz et al. | |
| 2014/0107668 A1 | 4/2014 | Zolotov | |
| 2015/0209220 A1 | 7/2015 | Lin | |
| 2019/0374243 A1 * | 12/2019 | Loff | A61B 17/322 |
| 2020/0113592 A1 | 4/2020 | Hayzlett et al. | |

FOREIGN PATENT DOCUMENTS

CN 108247726 7/2018

OTHER PUBLICATIONS

Non-Final Office Action for U.S. Appl. No. 15/866,833, dated Jan. 23, 2020.

(Continued)

*Primary Examiner* — Katherine H Schwiker
*Assistant Examiner* — Serenity A Miller
(74) *Attorney, Agent, or Firm* — Marcella M. Bodner; Cole Schotz, P.C.

(57) ABSTRACT

A device for separating a sample of tissue in a controlled and precise manner and, more particularly, to produce a piece of tissue having a generally planar configuration and, optionally, additional desired characteristics, such as a predetermined maximum thickness, and selected tissue type. The device is adjustable to allow for different thicknesses and different operational speeds for application to different types of recovered tissue samples.

19 Claims, 19 Drawing Sheets

(56) References Cited

OTHER PUBLICATIONS

Restriction Response for U.S. Appl. No. 15/866,833, dated Oct. 3, 2019.
U.S. Appl. No. 15/866,833, filed Jan. 10, 2018.
Final Office Action for U.S. Appl. No. 15/866,833, dated Jul. 28, 2020.
Issue Notification for U.S Pat. No. 11,185,346, issued on Nov. 10, 2021 for U.S. Appl. No. 15/866,833.
Notice of Allowance for U.S. Appl. No. 15/866,833, dated Aug. 3, 2021.
Non-Final Office Action for U.S. Appl. No. 15/866,833, dated Jan. 12, 2021.

* cited by examiner

TISSUE SEPARATION DEVICE AND METHODS FOR USING SAME

CROSS-REFERENCE TO RELATED APPLICATIONS

The present application claims the benefit of U.S. Provisional Application No. 62/888,831 filed on Aug. 19, 2019, the entire disclosure of which is hereby incorporated by reference herein.

FIELD OF THE INVENTION

The present invention relates generally to a device for separating a sample of tissue in a controlled and precise manner. More particularly, the tissue separation device cuts and separates a sample of tissue to produce a piece of tissue having a generally planar configuration and additional desired characteristics.

BACKGROUND OF THE INVENTION

Various tissue forms useful as grafts include processed tissue derived from samples of tissue which have been recovered from donors (live or deceased) and treated using one or more physical and chemical treatment techniques. Such tissue grafts are useful for tissue repair and reconstruction in recipients having tissue which is damaged, diseased, atrophied or which could otherwise benefit from such treatment, such as by cosmetic modification. Where the donor and the recipient are the same individual, the tissue graft is an autograft, and where they are different individuals of the same species, the tissue graft is an allograft. Where the donor and the recipient are different individuals of different species, then the tissue graft is a xenograft.

There is a wide variety of treatment techniques known and being developed for processing tissue samples into tissue grafts. The types of physical and chemical treatment techniques applied to a tissue sample, and the order in which they are applied, are selected based the properties desired for the resulting tissue graft which, in turn depends on the type of tissue to be treated, as well as the kind of damage, disease, or other condition of the tissue to be treated. In addition to the physical treatment required to recover tissue samples from donors, the physical treatment techniques employed frequently involve some form of separation, reshaping, or size reduction, and often include a combination of these techniques, sometimes in multiple or repeated steps.

In some circumstances, it is desired or useful to produce a piece of tissue having a generally planar shape and/or selected composition from a recovered tissue sample. The original recovered tissue sample may itself be generally planar or not and the physical treatment steps employed to produce the planar piece may be performed before, during or after other physical or chemical processing steps. Recovered tissue samples may comprise multiple layered tissue types, have a variable thickness, variable tissue density, or other variable characteristics. Tissue forms may be produced from such recovered tissue samples that comprise entirely or nearly entirely a single tissue type, or only specific selected tissue types, or more uniform characteristics such as thickness, density, etc.

The invention described herein provides a device and method of operation for the device for separating recovered tissue samples to produce a piece of tissue having a generally planar shape, a predetermined maximum thickness, and possibly one or more additional selected characteristics as mentioned above.

SUMMARY OF THE INVENTION

The present invention relates generally to a device for separating a sample of tissue in a controlled and precise manner and, more particularly, to produce a piece of tissue having a generally planar configuration and, optionally, additional desired characteristics, such as a predetermined maximum thickness, and selected tissue type. The device is adjustable to allow for different thicknesses and different operational speeds for application to different types of recovered tissue samples.

In an exemplary embodiment, a device is provided for producing a tissue product from a tissue sample, wherein the tissue product comprises a piece of tissue having a generally planar configuration and a predetermined maximum thickness between first and second surfaces thereof, the device comprising:

(A) a support base for supporting the device on a horizontal surface;

(B) a drum assembly mounted on the support base and comprising:
   a rotatable cylindrical drum having a longitudinal axis oriented parallel to the horizontal surface and an exterior cylindrical surface,
   a shaft extending through the drum coincident with the longitudinal axis, and
   a hand wheel mounted to the drum capable of manually rotating the drum;

(C) a drum motor assembly mounted to the support base and operably engaged with the shaft of the drum assembly and capable of continuously rotating the drum about the longitudinal axis;

(D) a blade assembly comprising a blade which is longitudinally aligned with and proximate to the exterior surface of the drum and capable of cutting a tissue sample mounted on the exterior surface to form the tissue product;

(E) a lateral movement mechanism operably engaged with and carrying the blade assembly and capable of moving the blade assembly reciprocatingly in a lateral direction;

(F) a lateral drive assembly operably engaged with and capable of operating the lateral movement mechanism to move the blade assembly reciprocatingly in a lateral direction, wherein the lateral movement mechanism, the lateral drive assembly, and the blade assembly are, together, capable of continuously cutting a tissue sample mounted on the exterior surface of the drum by reciprocatingly moving the blade assembly and blade thereof in the lateral direction;

(G) a blade motor assembly mounted to the support base and operably engaged with and capable of actuating the lateral drive assembly to operate the lateral movement mechanism; and (H) a thickness adjustment mechanism which is partially mounted on the support base and partially mounted to the lateral movement mechanism, thereby being operably engaged with the blade assembly, wherein the thickness adjustment mechanism is capable of setting the maximum predetermined thickness of the tissue product by moving the blade assembly in a linear direction, which is perpendicular to the longitudinal axis of the drum, and positioning the blade a distance from the exterior surface of the drum, wherein the distance is equal to maximum predetermined thickness of the tissue product.

In some embodiments, the thickness adjustment mechanism comprises:
- a block having a threaded bore and being mounted to the lateral movement mechanism which slidingly rests on two or more guide rails which enable movement of the lateral movement mechanism and the blade assembly carried thereon in the linear direction;
- a bearing block and adjacent seal plate which are fixedly mounted to the support base and have aligned threaded bores therethrough which are also aligned with the threaded bore of the block; and
- a threaded shaft having a knob at one end thereof, wherein the threaded shaft is threadedly received through and engaged with the threaded bores of each of the block, the bearing block and the seal plate, wherein the thickness adjustment mechanism is manually operable by turning the knob which moves the lateral movement mechanism and the blade assembly carried thereon in the linear direction and positions the blade a distance d from the exterior surface of the drum. In such embodiments, the device may further comprise one or more thickness setting plates for setting the distance between the blade of the blade assembly and the exterior surface of the drum, wherein each of the one or more thickness setting plates has a different respective thickness t and, when a selected one of the thickness setting plates is positioned between the knob and the seal plate, and the knob, the selected one of the thickness setting plates, and the seal plate are in contact with one another, the distance between the blade of the blade assembly and the exterior surface of the drum is equal to the respective thickness of the selected one of the setting plates.

In another exemplary embodiment, the device further comprises: (I) a tissue pusher assembly comprising a tissue pusher slidably mounted to the support base and which is longitudinally aligned with and proximate to the exterior surface of the drum, moveable in the same linear direction as, and independently of, the thickness adjustment mechanism, and capable of pressing and holding a tissue sample on the exterior surface during operation of the device. In such embodiments, the (I) tissue pusher assembly may further comprise:
- at least one post mounted to the support base;
- a plate mounted to the at least one post at a fixed elevation above the support base and having at least two threaded holes;
- a slotted extension which extends from a side of the tissue pusher opposite the drum and has two or more slots, each of which is sized and shaped to align with a corresponding one of the at least two threaded holes of the plate; and
- two or more knobs each having a threaded shaft sized and shaped to be threadedly received, through a respective one of the two or more slots, and in a respective one of the at least two threaded holes of the plate, whereby the tissue pusher and slotted extension are slidably movable together, in the same linear direction as, but independently of, the thickness adjustment mechanism, and secured in a fixed position by turning the two or more knobs until tight.

The present invention also provides a method for producing a tissue product from a tissue sample using the aforesaid device, wherein the tissue product comprises a piece of tissue having a generally planar configuration and a predetermined maximum thickness between first and second surfaces thereof. In an exemplary embodiment, the method comprises the sequential steps of:

(A) optionally, modifying the tissue sample to have a size and shape suitable for use with the device (B) mounting the tissue sample on the exterior surface of the drum;

(C) selecting and setting the maximum predetermined thickness of the tissue product by positioning the blade of the blade assembly a distance d from the exterior surface of the drum, using the thickness adjustment mechanism;

(D) positioning the tissue sample in a suitable position relative to the blade of the blade assembly by manually rotating the drum using the hand wheel, wherein the suitable position is when a leading edge of the tissue sample is proximate to but not yet in contact with the blade;

(E) commencing lateral reciprocating movement of the blade assembly by supplying power to the blade motor assembly, which actuates the lateral drive assembly, which operates the lateral movement mechanism, which moves the blade assembly reciprocatingly in the lateral direction;

(F) commencing rotation of the drum and the tissue sample mounted on the exterior surface thereof by supplying power to the drum motor assembly;

(G) allowing the concurrent reciprocating movement of the blade assembly and rotation of the drum and the tissue sample mounted on the exterior surface thereof to continue until all of the tissue sample has passed by the blade assembly to form a first tissue product which remains on the drum and a second piece of tissue which has been separated from the first tissue product;

(H) optionally, removing the first tissue product from the drum, wherein the first tissue product has a generally planar configuration, a predetermined maximum thickness, and, optionally, consists essentially of a selected tissue type;

(I) optionally, removing the first tissue product from the drum and mounting the second piece of tissue to the exterior surface of the drum as a next tissue sample to be cut, and repeating steps (C) to (G); and (J) optionally, leaving the first tissue product on the drum and using the first tissue product as a next tissue sample to be cut, and repeating steps (D) to (G).

For embodiments in which the device further comprises the aforesaid (I) a tissue pusher assembly, additional exemplary embodiments of the method may further comprise:

after the step of (B) mounting the tissue sample on the exterior surface of the drum, and before the steps of (E) commencing lateral reciprocating movement of the blade assembly and (F) commencing rotation of the drum and the tissue sample mounted on the exterior surface thereof, positioning the tissue pusher at a desired position and distance from the tissue sample whereby the tissue pusher presses and holds the tissue sample on the exterior surface of the drum.

Other exemplary embodiments of the method for producing a tissue product from a tissue sample using the aforesaid device, where the thickness adjustment mechanism comprises the aforesaid elements (e.g., a block having a threaded bore and being mounted to the lateral movement mechanism which slidingly rests on two or more guide rails, a bearing block and adjacent seal plate, and a threaded shaft having a knob at one end thereof, wherein the threaded shaft is threadedly received through and engaged with the threaded bores of each of the block, the bearing block and the seal plate) which enables manual operation of the thickness adjustment mechanism as described above, and where the device further comprises one or more thickness setting plates for setting the distance between the blade of the blade assembly and the exterior surface of the drum, as also described above, the method comprises the sequential steps of:

(A) optionally, modifying the tissue sample to have a size and shape suitable for use with the device (B) mounting the tissue sample on the exterior surface of the drum;

(C) selecting and setting the maximum predetermined thickness of the tissue product, using the thickness adjustment mechanism and a selected one of the one or more thickness setting plates, by selecting one of the one or more thickness setting plates, positioning the selected one thickness setting plate between the knob and the seal plate, turning the knob, until the knob, the selected one thickness setting plate, and the seal plate are in contact with one another, thereby positioning the blade of the blade assembly a distance from the exterior surface of the drum, whereby that the distance between the blade and the exterior surface of the drum is equal to the respective thickness of the selected one thickness setting plate;

(D) positioning the tissue sample in a suitable position relative to the blade of the blade assembly by manually rotating the drum using the hand wheel, wherein the suitable position is when a leading edge of the tissue sample is proximate to but not yet in contact with the blade;

(E) commencing lateral reciprocating movement of the blade assembly by supplying power to the blade motor assembly, which actuates the lateral drive assembly, which operates the lateral movement mechanism, which moves the blade assembly reciprocatingly in the lateral direction;

(F) commencing rotation of the drum and the tissue sample mounted on the exterior surface thereof by supplying power to the drum motor assembly;

(G) allowing the concurrent reciprocating movement of the blade assembly and rotation of the drum and the tissue sample mounted on the exterior surface thereof to continue until all of the tissue sample has passed by the blade assembly to form a first tissue product which remains on the drum and a second piece of tissue which has been separated from the first tissue product;

(H) optionally, removing the first tissue product from the drum, wherein the first tissue product has a generally planar configuration, a predetermined maximum thickness, and, optionally, consists essentially of a selected tissue type;

(I) optionally, removing the first tissue product from the drum and mounting the second piece of tissue to the exterior surface of the drum as a next tissue sample to be cut, and repeating steps (C) to (G); and (J) optionally, leaving the first tissue product on the drum and using the first tissue product as a next tissue sample to be cut, and repeating steps (D) to (G).

In some exemplary embodiments of the aforesaid methods, the tissue sample comprises dermal tissue.

In some exemplary embodiments of the aforesaid methods, the tissue product has a generally planar configuration and a predetermined maximum thickness. Furthermore, the tissue product may comprise a selected tissue type. In some embodiments, the tissue product consists essentially of a selected tissue type. In some embodiments, the tissue sample comprised processed dermal tissue, and the tissue product consists essentially of reticular dermis and, optionally, at least a portion of papillary dermis.

BRIEF DESCRIPTION OF THE DRAWINGS

The present invention will be further explained with reference to the attached drawings, wherein like structures are referred to by like numerals and/or letters throughout the several views. The drawings shown are not necessarily to scale, with emphasis instead generally being placed upon illustrating the principles of the present invention.

DETAILED DESCRIPTION OF THE INVENTION

Figure 1:
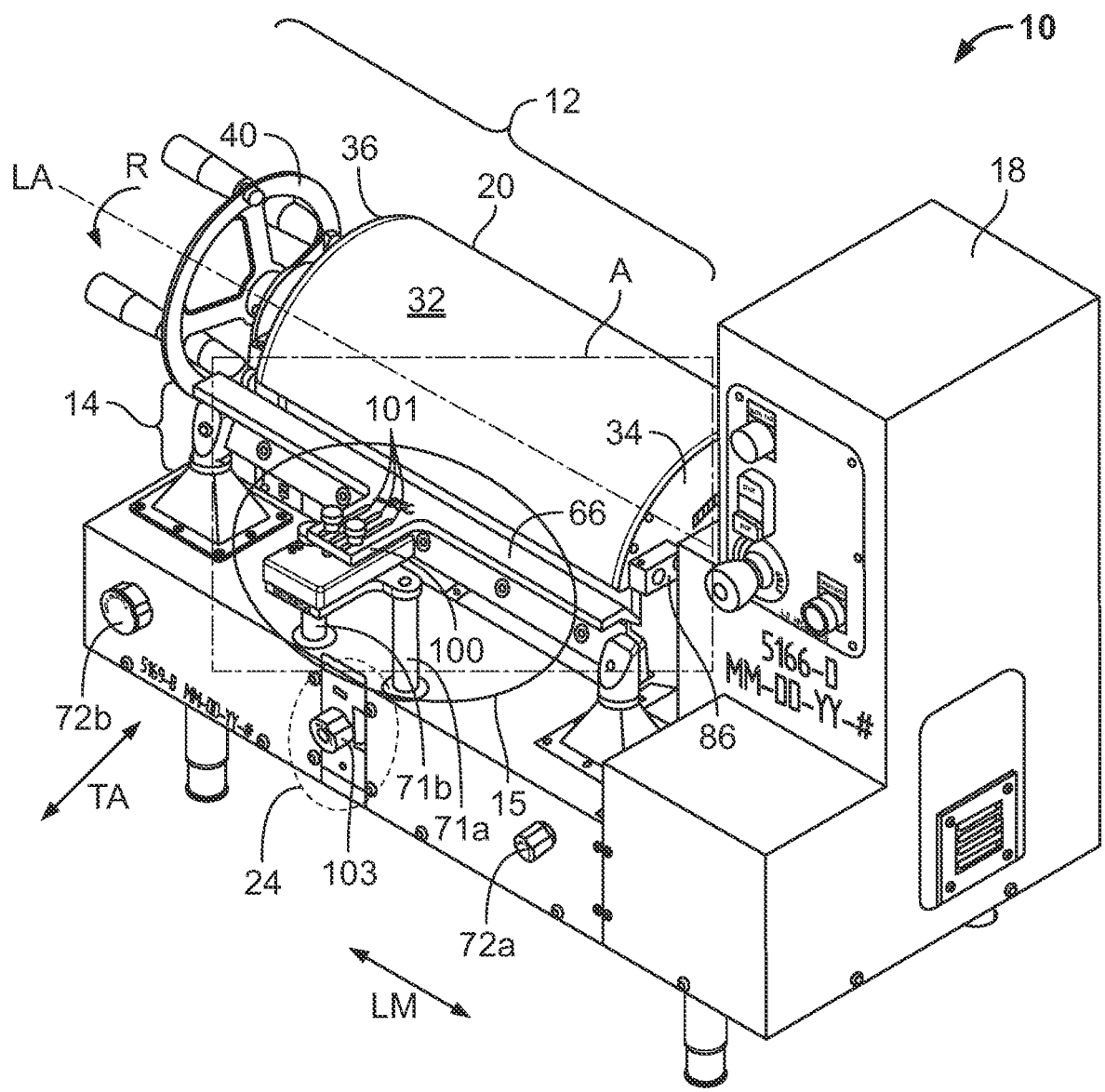
FIG. 1 is a front elevational perspective view of an exemplary tissue separation device in accordance with the invention described herein.

Detailed descriptions of one or more embodiments of the present invention are disclosed herein. It should be understood that the disclosed embodiments are merely illustrative of the invention which may be embodied in various forms. In addition, each of the examples given in connection with the various embodiments of the invention is intended to be illustrative, and not restrictive. Further, the figures are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as examples for teaching one skilled in the art to variously employ the present invention.

The tissue separation device according to the present invention is applied to a tissue sample to produce a planar tissue form useful as a graft to treat diseased, damaged or atrophied tissue, or tissue having undesirable qualities, such as wrinkles or unattractive contours. The tissue separation device has multiple adjustable and moving components, as well as control and automation features, which are arranged and cooperate with one another to enable an operator to precisely cut and separate a tissue sample into at least two portions or pieces, at least one of which is a planar tissue form useful as a graft.

The planar tissue form produced by the tissue separation device has a desired predetermined maximum thickness and, optionally, additional selected characteristics. The thickness and other characteristics are selected by persons of ordinary skill in the relevant art based on the general knowledge possessed by such persons together with the particular intended use for the tissue graft, such as what type of tissue and/or condition is to be treated, where in or on the recipient the graft will be placed or implanted, and the desired results of the treatment. In addition to the planar tissue form, one or more other portions or pieces produced from the tissue sample may also be useful as a graft material, may be useful for another purpose, or may be discarded.

The tissue sample to which the tissue separation device is applied is typically recovered from a donor, either living or deceased, and which may be human or non-human. Depending on the donor, the tissue graft produced from the recovered tissue sample may be an autograft, allograft or xenograft. Furthermore, while not necessarily limited, the tissue separation device is best adapted for use with generally planar tissue samples of virtually any type of tissue.

The term "planar" means that the tissue (whether a recovered tissue sample or a tissue form produced therefrom) has an easily discernable top surface and an oppositely oriented, easily discernable bottom surface with a thickness therebetween and one or more edges extending around the perimeter and contacting both of the top and bottom surfaces. In some embodiments, the planar tissue has broad, flat, continuous top and bottom surfaces which are generally parallel to one another. However, the top and bottom surfaces of planar tissue need not be parallel. Shapes typically understood to be "planar" and particularly suitable for use with the presently described tissue separation device include, for example without limitation, sheets, membranes, bricks, blocks, strips, wedges, panes, panels, slabs, plates, etc., with a minimum length or width of the top and bottom surfaces being at least about 5 times, such as at least about 8 times, or at least about 10 times, or at least about 15 times, or at least about 20 times the thickness of the planar tissue.

The original recovered tissue sample may itself be generally planar or not and the use of the tissue separation device described herein to produce a planar tissue form from the tissue sample may be performed before, during or after other physical or chemical processing steps. Sometimes the recovered tissue sample comprises multiple layered tissue types and it is desired to separate and recover a layer comprising entirely or nearly entirely a single tissue type, or only specific selected tissue types. In other cases, the recovered tissue sample may have a variable thickness, variable tissue density, or other variable characteristics which may be made more uniform by shaping or cutting the recovered tissue sample into one or more planar tissue pieces using the tissue separation device described herein. In still other cases, the intended use of the resulting tissue graft would be facilitated or enhanced by reshaping, cutting, or separating the initial recovered tissue sample to produce a generally planar piece of tissue.

The types of tissue suitable for use with the tissue separation device are any tissue types which are either naturally, or can be shaped to be, generally planar, such as, without limitation, dermis, adipose, muscle (especially smooth muscle), umbilical cord, bone (cancellous or at least partially demineralized cortical bone), and cartilage. In some embodiments, the recovered tissue sample may comprise more than one type of tissue, such as a recovered sample of dermis with adipose or a recovered sample of bone with cartilage.

Figure 24:
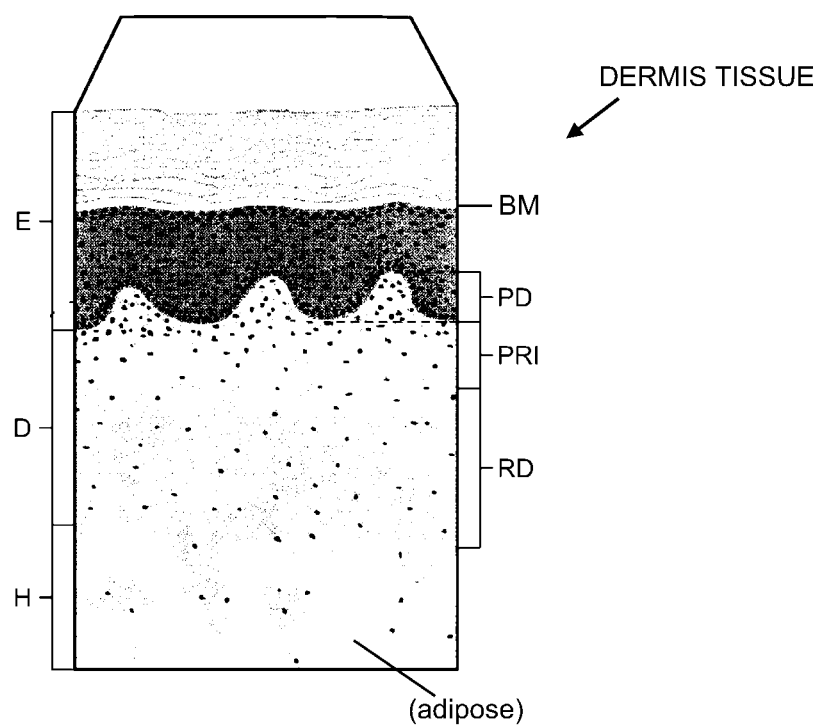
FIG. 24 is an enlarged cross-section view of a portion of an exemplary dermis tissue sample showing its layers and components.

Furthermore, in some embodiment, the recovered tissue sample may be a type of tissue which endogenously also comprises layers of different types of tissue. For example, without limitation, a recovered sample of dermis tissue (see, e.g., FIG. 24) typically includes epidermis (E) and dermis (D) layers, with a basement membrane (BM) therebetween, and furthermore, the dermis layer (D) includes papillary dermis layer (PD) and a deeper reticular dermis layer (RD) with a papillary-reticular interface (PRI) between the papillary and reticular dermis layers (PD, RD). In some embodiments, a dermis tissue sample may also include a hypodermis layer (H) beneath the reticular dermis layer (RD) or the dermis (D) and adipose tissue may be present in the hypodermis layer (H). For purposes of the present disclosure dermis tissue is representative of a typical planar tissue sample.

In some embodiments, the planar tissue form produced by application of the tissue separation device to a tissue sample has a uniform maximum thickness such that the top and bottom surfaces are relatively flat or smooth and parallel to one another. In some embodiments, the planar tissue form produced from a tissue sample consists entirely or nearly entirely of a single tissue type, such as a planar tissue form derived from a dermis tissue sample and including only epidermis (E), or only dermis (D) layer, both papillary dermis (PD) and dermis (D) layers In some circumstances, it is desired or useful to produce a piece of tissue having a generally planar shape and/or selected composition from a recovered tissue sample. The original recovered tissue sample may itself be generally planar or not and the physical treatment steps employed to produce the planar tissue form may be performed before, during or after other physical or chemical processing steps. Sometimes the recovered tissue sample comprises multiple layered tissue types and it is desired to separate and recover a layer comprising entirely or nearly entirely a single tissue type, or only specific selected tissue types. In other cases, the recovered tissue sample may have a variable thickness, variable tissue density, or other variable characteristics which may be made more uniform by shaping or cutting the recovered tissue sample into one or more planar tissue pieces. In still other cases, the intended use of the resulting tissue graft would be facilitated or enhanced by reshaping, cutting, or separating the initial recovered tissue sample to produce a generally planar piece of tissue. Other various compositions for the planar tissue form will be readily envisioned and designed by persons of ordinary skill in the relevant art.

The tissue separation device will now be described in detail, with reference to FIGS. 1-19. First a general overview introducing the major components and assemblies of the tissue separation device will be provided, as well as more detailed description of the relevant constituent parts of each of the major assemblies and how they are arranged and cooperate with each other. Where detailed description of a component, its purpose or operation, or the manner of its connection to other components, are not specifically described herein, such components, their purpose, operation and connection to other components, are deemed to be conventional and well within the ability of persons of ordinary skill to select, install and operate in connection with the components and assemblies of the tissue separation device and method for its use which are described in detail herein. Finally, a description is provided of a particular embodiment of the device which is mounted on a wheeled cart and operated using a foot switch controller, along with an explanation of how the device is operated to process a recovered tissue sample to produce a planar tissue form suitable for use as a graft.

Figure 2:
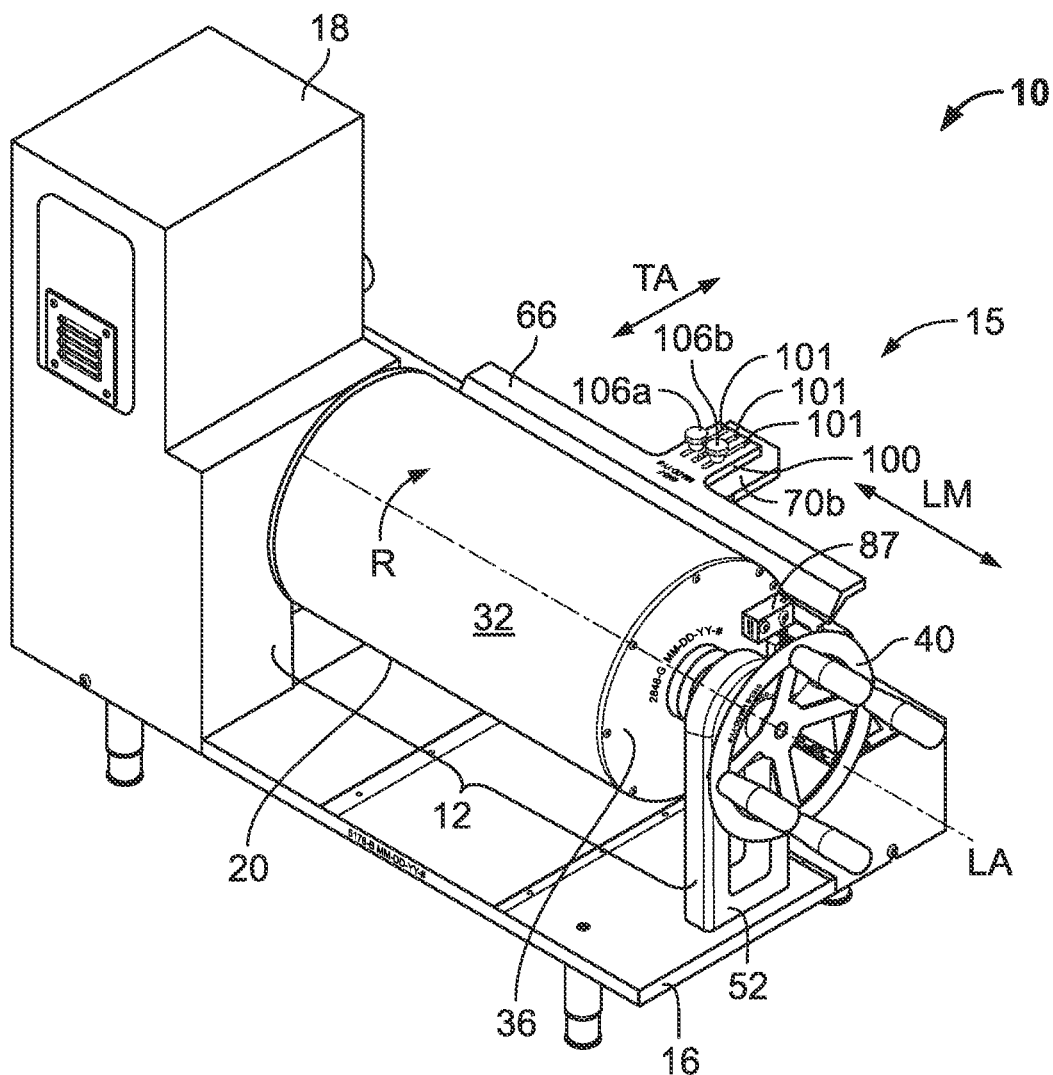
FIG. 2 is a rear elevational perspective view of the tissue separation device of FIG. 1 in which the support base is visible.
Figure 3:
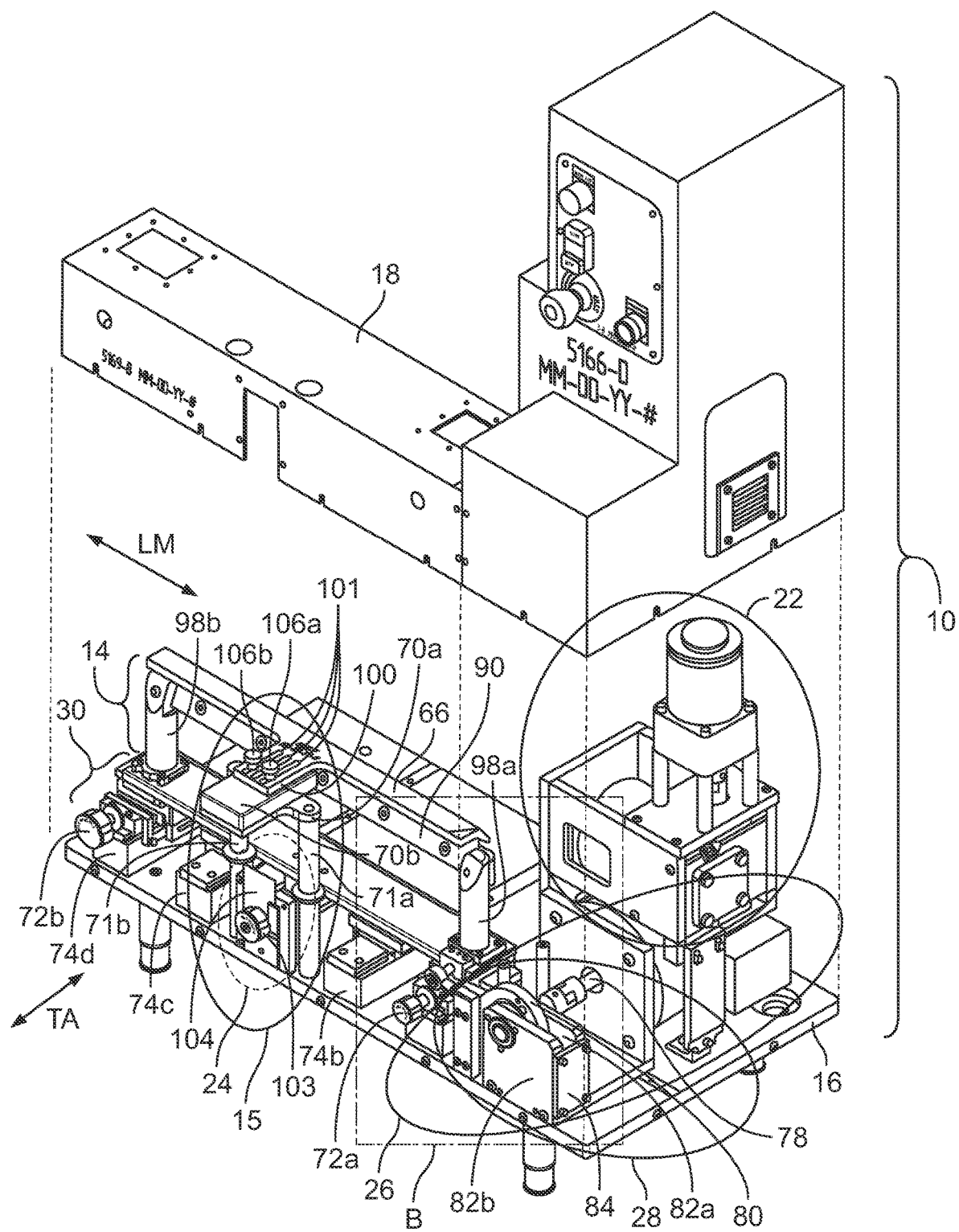
FIG. 3 is an exploded front perspective view of the device of FIG. 1, without the drum assembly and showing the housing separated from operational components mounted on the support base.

With reference now to FIGS. 1-3, the major components and assemblies of an exemplary embodiment of a tissue separation device 10 will now be described. The front and rear elevational perspective views of FIGS. 1 and 2 show an exemplary embodiment of a tissue separation device 10 which includes a drum assembly 12, a blade assembly 14 and a tissue pusher assembly 15, mounted proximate one another on a support base 16, as well as a housing 18 which covers and conceals several additional operational components of the device 10. As will be described in further detail below, during operation, the blade assembly 14 is for cutting a planar tissue sample (not shown in FIGS. 1-3, but see FIGS. 10 and 11A) mounted on the drum 20 of the drum assembly 12 to form and separate a piece of tissue (not shown) from the planar tissue sample. The drum 20 is rotated about its longitudinal axis LA and consequently also moves the tissue sample relative to the blade assembly 14 to accomplish the aforesaid cutting and separating. The tissue pusher assembly 15 presses and holds the tissue sample on the drum 20 as the drum 20 is rotated, to ensure that the leading edge of the tissue sample contacts and is precisely cut to a desired thickness by the blade assembly 14.

FIG. 3 provides an exploded perspective view of the tissue separation device 10, without the drum assembly 12 and with the housing 18 lifted to reveal the additional operational components of the device 10 mounted to the support base 16. More particularly, additional operational components of the device 10 include a drum motor assembly 22 mounted to the support base 16. The drum motor assembly 22 is operably engaged with the drum 20 of the drum assembly 12 for rotating the drum 20 and any tissue sample (not shown) mounted thereon, about the longitudinal axis LA and in the direction of the arrow R shown in FIGS. 1 and 2 (and also in FIGS. 4, 6, 8A-11B).

Additional operational components of the device 10 also include a thickness adjustment mechanism 24 mounted to the support base 16 and operably engaged with the blade assembly 14. More particularly, the thickness adjustment mechanism 24 is indicated with a dotted oval in each of FIGS. 3 and 14-16 and with a dash-dot square in FIG. 12. The thickness adjustment mechanism 24 is manually operated and moves the blade assembly 14 linearly in the direction of the arrow TA shown in FIGS. 1-3 (and also in FIGS. 9-15). As explained in further detail below, the thickness adjustment mechanism 24 moves the blade assembly 14 to a specified distance from the drum 20, and the blade assembly 14 is locked in position using the locking knobs 72a and 72b. Accordingly, using the thickness adjustment mechanism 24, the blade assembly 14 is movable between positions that are closer to and farther from the drum assembly 12 and can be held in any such position at a selected distance from the drum assembly 12 using the locking knobs 72a, 72b. When a tissue sample (not shown, but see FIGS. 10 and 11A) is mounted on the drum 20 of the drum assembly 12, the aforesaid arrangement enables an operator to select and control the thickness of a piece of tissue which is precisely cut and separated from the tissue sample by the blade assembly 14. As will become apparent from description provided below, it is possible that the desired planar tissue form (not shown) being produced from the tissue sample may be either the piece of tissue that is cut and separated, or all or a portion of the tissue sample remaining mounted on the drum 20.

As also shown in FIG. 3, the tissue separation device 10 further includes a blade motor assembly 26 mounted to the support base 16 and operationally engaged with a lateral drive assembly 28, which is also mounted to the support base 16 and is operably engaged with a lateral movement mechanism 30 which is, in turn, also mounted to the support base 16 and is operably engaged with the blade assembly 14.

In addition to moving closer to and further from the drum 20, the blade assembly 14 is also capable of lateral reciprocating movement to perform the cutting of the tissue sample mounted on the drum 20. The blade motor assembly 26 actuates the lateral drive assembly 28 which operates the lateral movement mechanism 30 which, in turn, moves the blade assembly 14 reciprocatingly in the direction of the arrow LM shown in FIGS. 1-3 (and also FIGS. 9, 12, 15 and 17), for a maximum total distance of about 2.54 centimeters. Accordingly, when a tissue sample (not shown, but see tissue sample T in FIGS. 10 and 11A) is mounted on the drum 20 of the drum assembly 12 and held thereon by the tissue pusher assembly 15, the aforesaid arrangement and lateral reciprocating movement of the blade assembly 14 performs the precise and continuous cutting of the tissue sample. The automation of a continuous reciprocating lateral movement of the blade assembly 14 eliminates the inherent variability of manual operation, thereby improving the precision of the cutting and separation of the tissue sample.

The tissue pusher assembly 15 of the tissue separation device 10 includes a tissue pusher 66 operably mounted to the support base 16. The pusher assembly 15 is also manually operated and moves the tissue pusher 66 linearly in the direction of the arrow TA shown in FIGS. 1-3 (as will be described in further detail below with reference to FIGS. 9, 10, 11A, 11B and 15). The pusher assembly 15 is capable of holding or locking the tissue pusher 66 at a selected position. Accordingly, the tissue pusher 66 is movable between positions that are closer to and farther from the drum assembly 12 and can be held in any such position at a selected distance from the drum assembly 12. When a tissue sample (not shown, but see FIGS. 10 and 11A) is mounted on the drum 20 of the drum assembly 12, and the drum 20 is rotated in the direction shown by the arrow R, the aforesaid arrangement enables an operator to select a position for the tissue pusher 66 which enables it to cooperate with the blade assembly 14 and continuously hold the tissue sample against the drum 20 as the drum 20 is rotated and the tissue sample is being cut by the blade assembly 14. As will be apparent from the description provided below, it is possible that the desired planar tissue form (not shown) being produced from the tissue sample may be either the piece of tissue that is cut and separated, or a portion of the tissue sample remaining mounted on the drum 20 after a cutting operation.

With reference now to FIGS. 4-9, the drum assembly 12 will now be described in further detail. As already explained above, the drum assembly 12 includes a drum 20 which is rotatable about its longitudinal axis LA. Additionally, as shown particularly in FIGS. 4 and 6, the drum 20 is partially hollow and cylindrical with an exterior cylindrical surface 32 and right and left end plates 34, 36 enclosing the partially hollow interior 38. The drum width W (see FIGS. 4 and 7) is the shortest distance from one end plate 34 to the other 36 as measured on the exterior surface 32 of the drum 20. The drum width W is typically at least about 20 centimeters (cm), such as at least about 30 cm, or at least about 40 cm, or less than about 60 cm, or less than about 50 cm, or less than about 40 cm, or less than about 30 cm. The drum assembly 12 also includes a hand wheel 40 affixed to the left end plate 36 for optional manual rotation of the drum 20.

A shaft 42 extends through the drum 20, coincident with the longitudinal axis LA. One end 44 of the shaft 42 extends out of the drum 20, through a center opening 46 (see FIG. 6) provided in the right end plate 34, and into engagement with the drum motor assembly 22 (not shown per se) for rotating the drum 20. The opposite end 48 of the shaft 42 extends out of the drum 20, through a center opening 50 (see FIG. 6) provided in the left end plate 36. An upright bracket 52 mounted to the support base 16 has an opening 54 (see FIG. 6) for rotatably receiving the opposite end 48 of the shaft 42 therein, thereby rotatably supporting the drum 20 above the support base 16.

Figure 4:
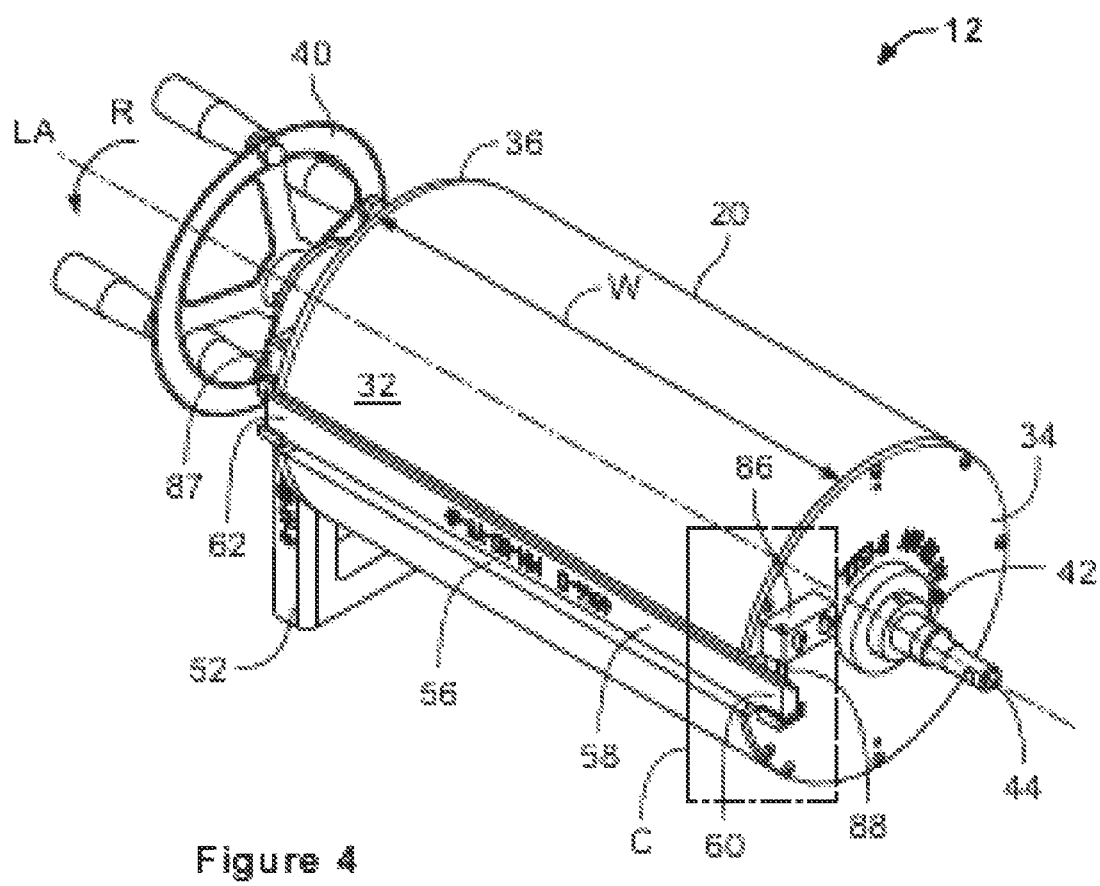
FIG. 4 is a is a front elevational perspective view of the drum assembly of the device of FIG. 1.
Figure 5:
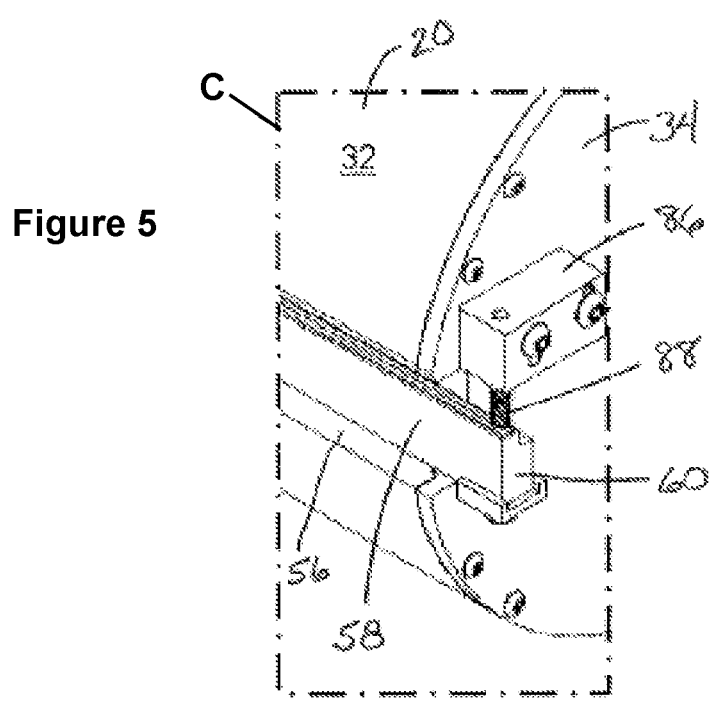
FIG. 5 is an enlarged view of the components shown in area C in FIG. 4 bounded by dash-dot lines, providing a detailed view of one end of the tissue clamp as it is pivotably fastened to the drum.
Figure 6:
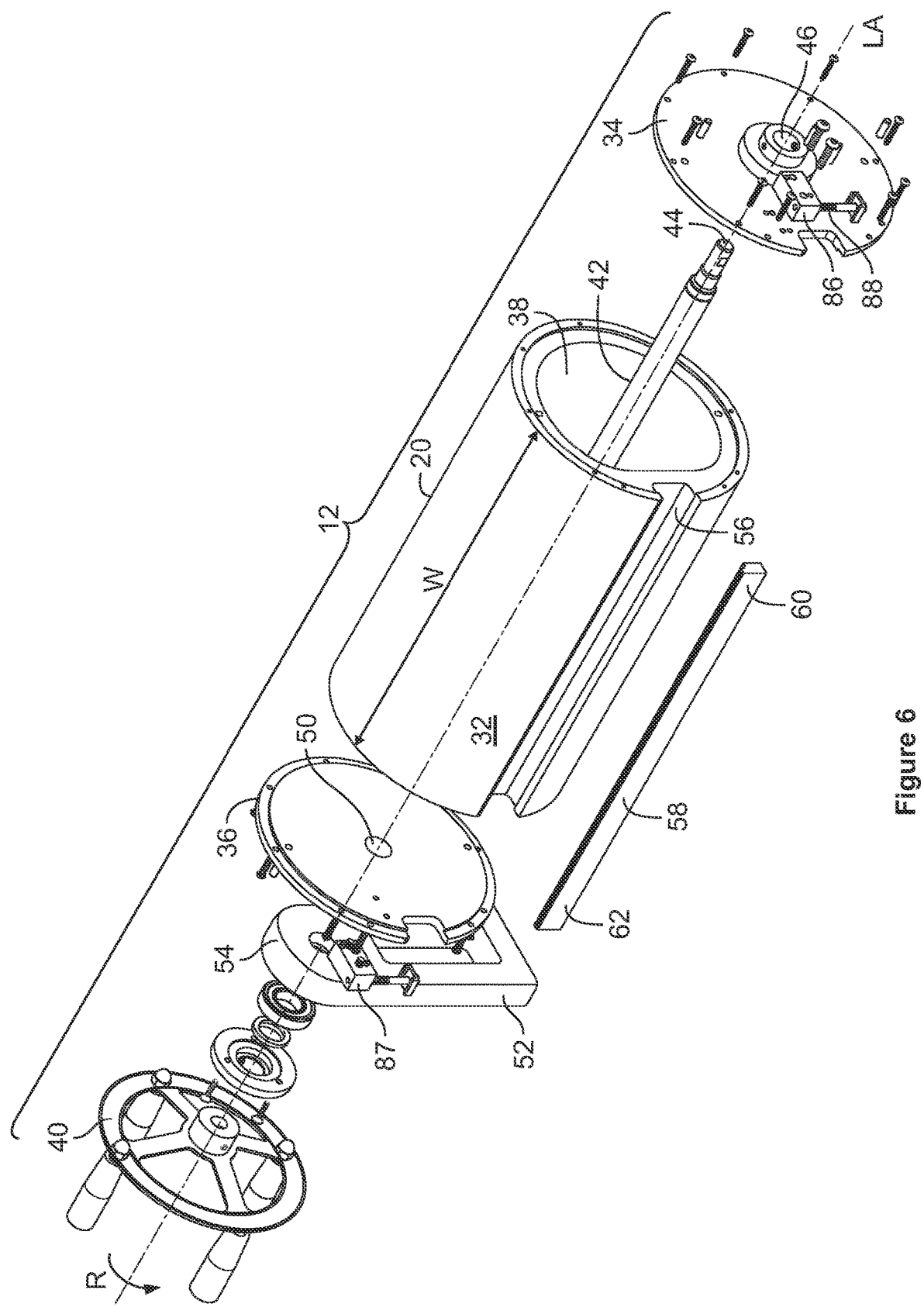
FIG. 6 is an exploded perspective view of the drum assembly of FIG. 4.

As can be seen most clearly in FIGS. 4-8B (and also in FIGS. 10-11B), the drum 20 has a longitudinally oriented groove 56 for receiving an edge TE of a planar tissue sample T (see FIGS. 10 and 11A) therein and facilitating mounting the planar tissue sample T on the exterior surface 32 of the drum 20 for processing. The drum assembly 12 also includes a tissue clamp 58 which is sized and shaped to be received in the groove 56, on top of the edge TE of the tissue sample T inserted in the groove 56 (see FIGS. 10 and 11A) to retain the edge TE of the tissue sample T in the groove 56. The tissue clamp 58 is pivotably connected at one end 60 thereof with a connector, such as a pin or screw 88, to one of the end plates, such as the right end plate 34, proximate one end of the groove 56, as shown in FIGS. 4-5 and 7-9. This pivotable connection is more clearly shown in FIG. 5 which is an enlargement of the components within the dash-dot lines of area C in FIG. 4. As shown in FIG. 5 (as well as FIGS. 7-11B), a pivotable connection between one end 60 of the tissue clamp 58 may be formed using an alignment block 86 affixed to the right end plate 34 and a pin or screw 88 inserted through openings (not shown) in both the alignment block 86 and the one end 60 of the tissue clamp 58.

Figure 7:
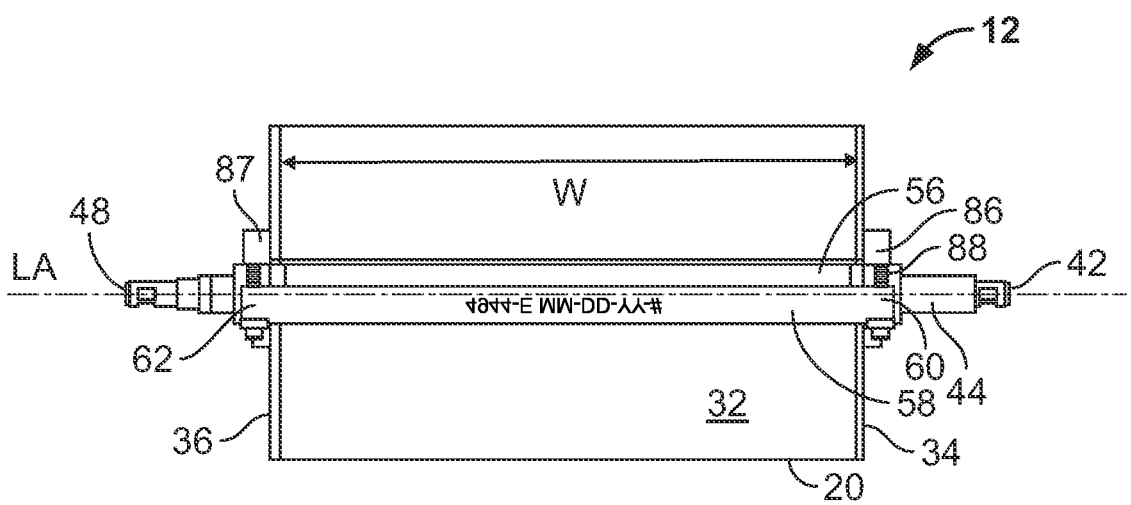
FIG. 7 is an elevational front plan view of the drum assembly of FIG. 4 without the upright support bracket and hand wheel, and showing the tissue clamp in its closed position in the groove of the drum.
Figure 8A:
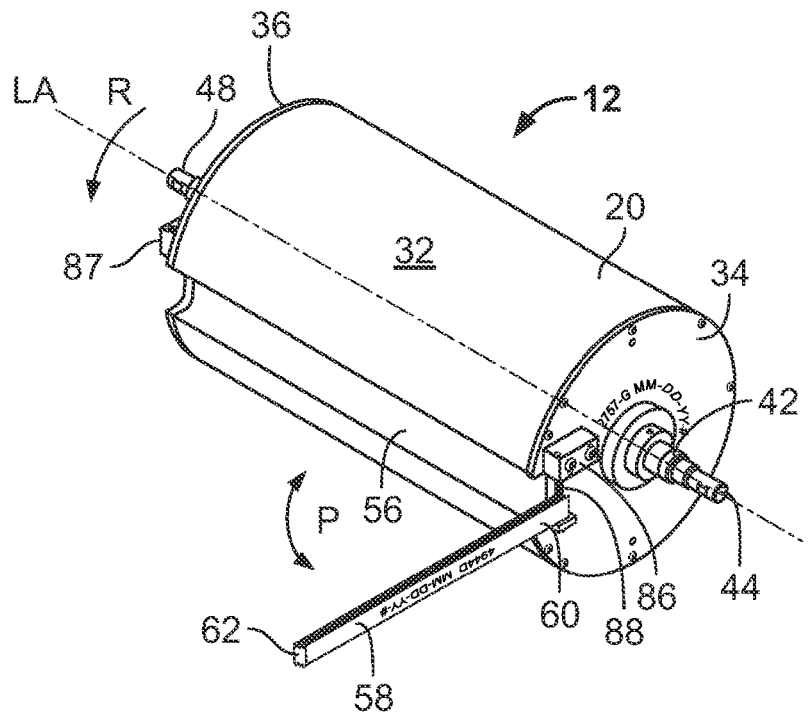
FIG. 8A is a front elevational perspective view of the drum of FIG. 7 showing the tissue clamp in an open position.
Figure 8B:
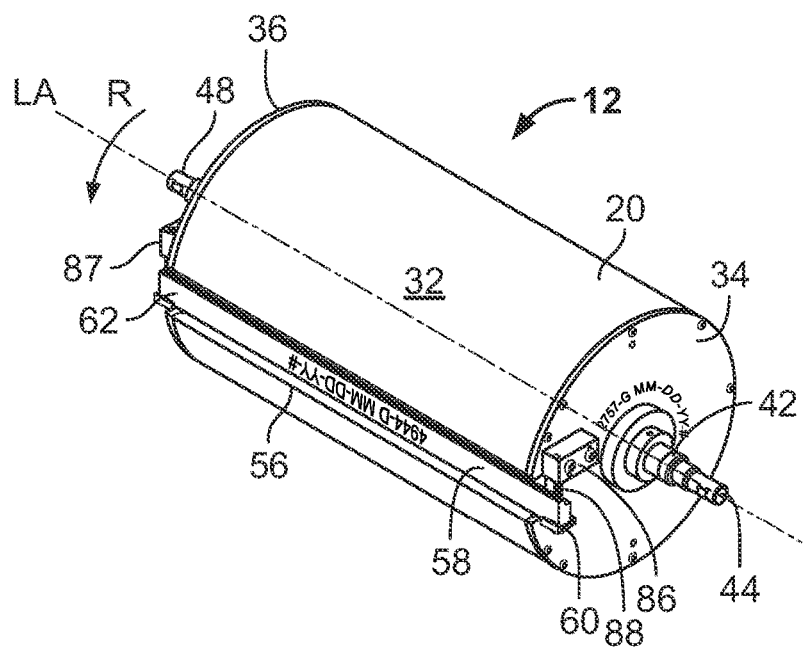
FIG. 8B is a front elevational perspective view of the drum of FIG. 8A showing the tissue clamp in its closed position.
Figure 9:
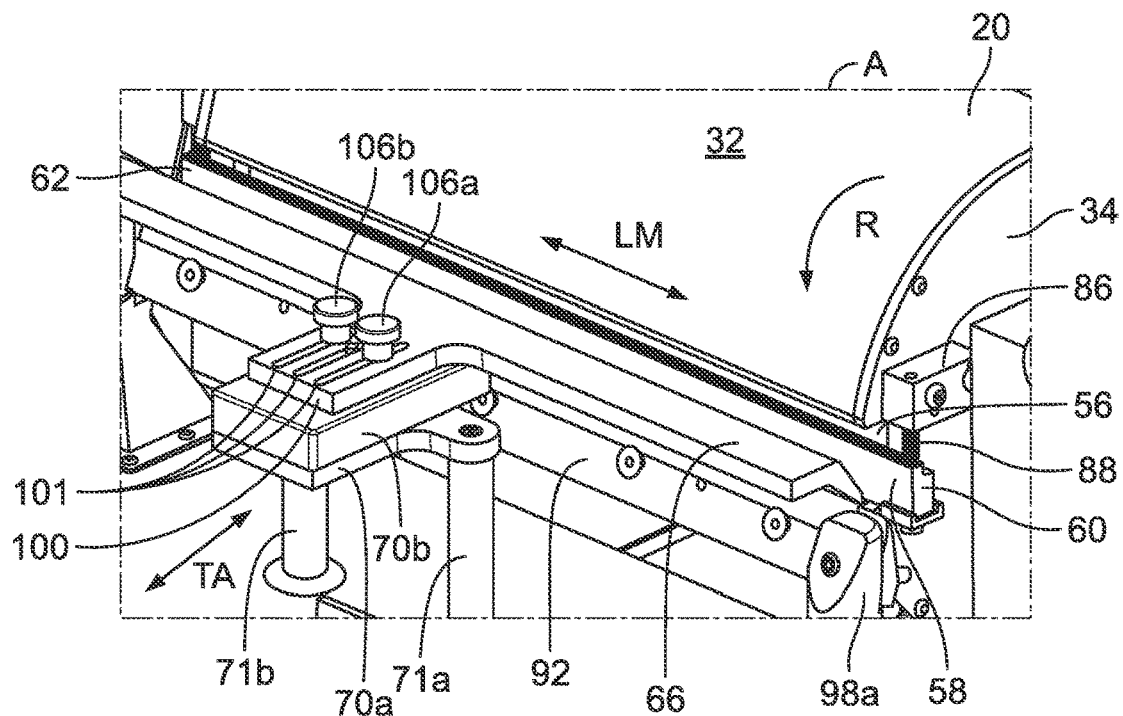
FIG. 9 is an enlarged view of the components shown in area A in FIG. 1, bounded by dash-dot lines, providing a detailed view of the blade assembly and the tissue pusher assembly positioned proximate to the drum.

The foregoing configuration allows the tissue clamp 58 to be movable, in the directions indicated by the arrow P in FIG. 8A, between any of several open positions, such as that shown in FIG. 8A in which the tissue clamp 58 is outside the groove 56, and its closed position shown in FIGS. 4, 7, 8B and 9, in which the entire length of the tissue clamp 58 is seated within the groove 56. In its closed position, the tissue clamp 58 retains the edge TE of the planar tissue sample T in the groove 56 (see FIGS. 10 and 11A) during rotation of the drum 20 in the direction of the arrow R. As shown in FIGS. 4, 7 and 8B, the tissue clamp 58 may be kept in its closed position by connecting an opposite end 62 of the tissue clamp 58 to the other (e.g., left) end plate 36 using another alignment block 87 affixed to the left end plate 36. With the foregoing configuration of components, the drum assembly 12 holds a planar tissue sample T mounted on the exterior surface 32 of the drum 20 and, when the drum 20 is rotated in the direction of the arrow R, a continuously advancing leading edge TE of the tissue sample T is provided for contact with the blade assembly 14, as will be described below.

Figure 15:
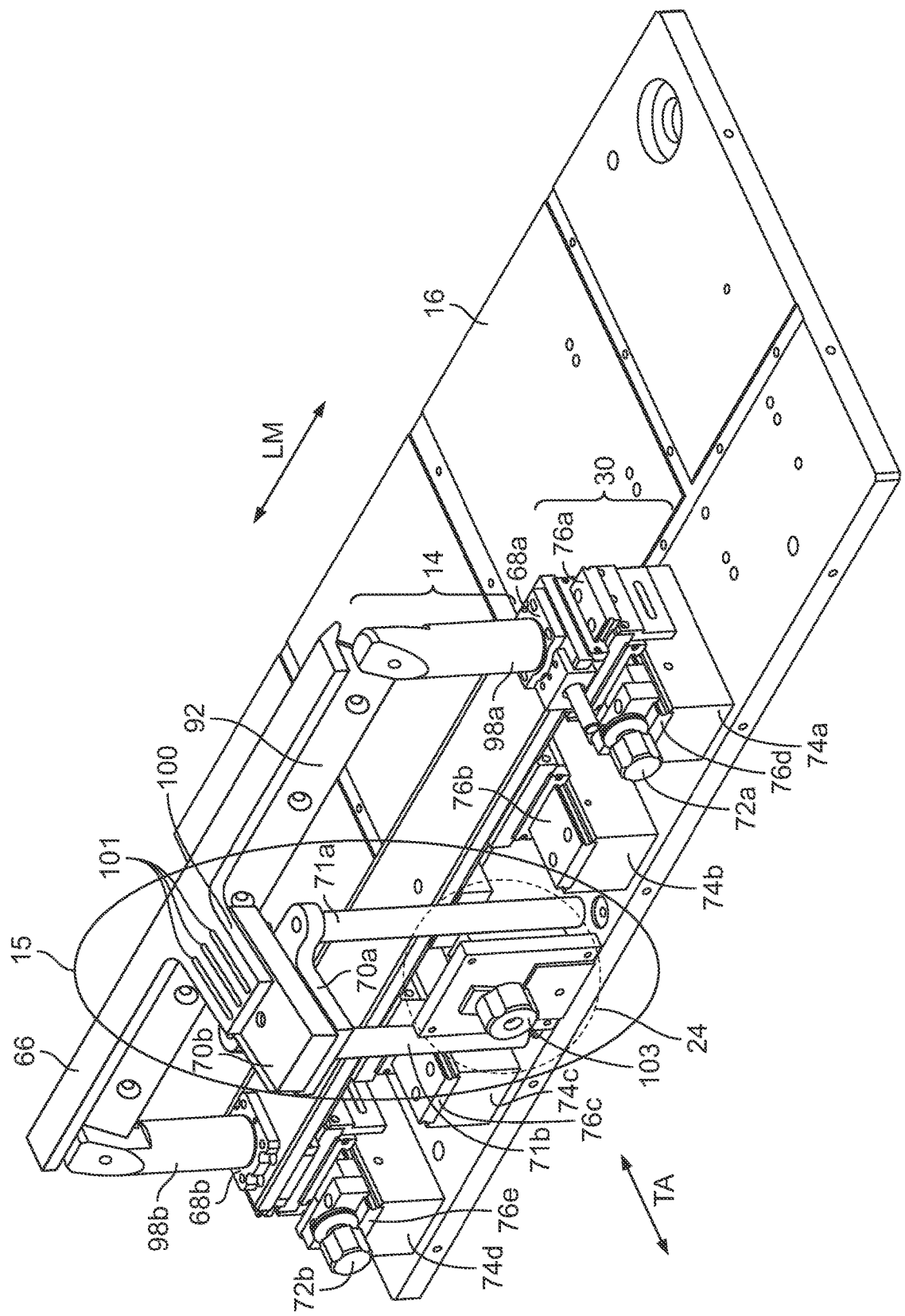
FIG. 15 is a front elevational perspective view of the blade assembly and its lateral movement and thickness adjustment mechanisms, as well as the tissue pusher assembly, all mounted on the support base.
Figure 16:
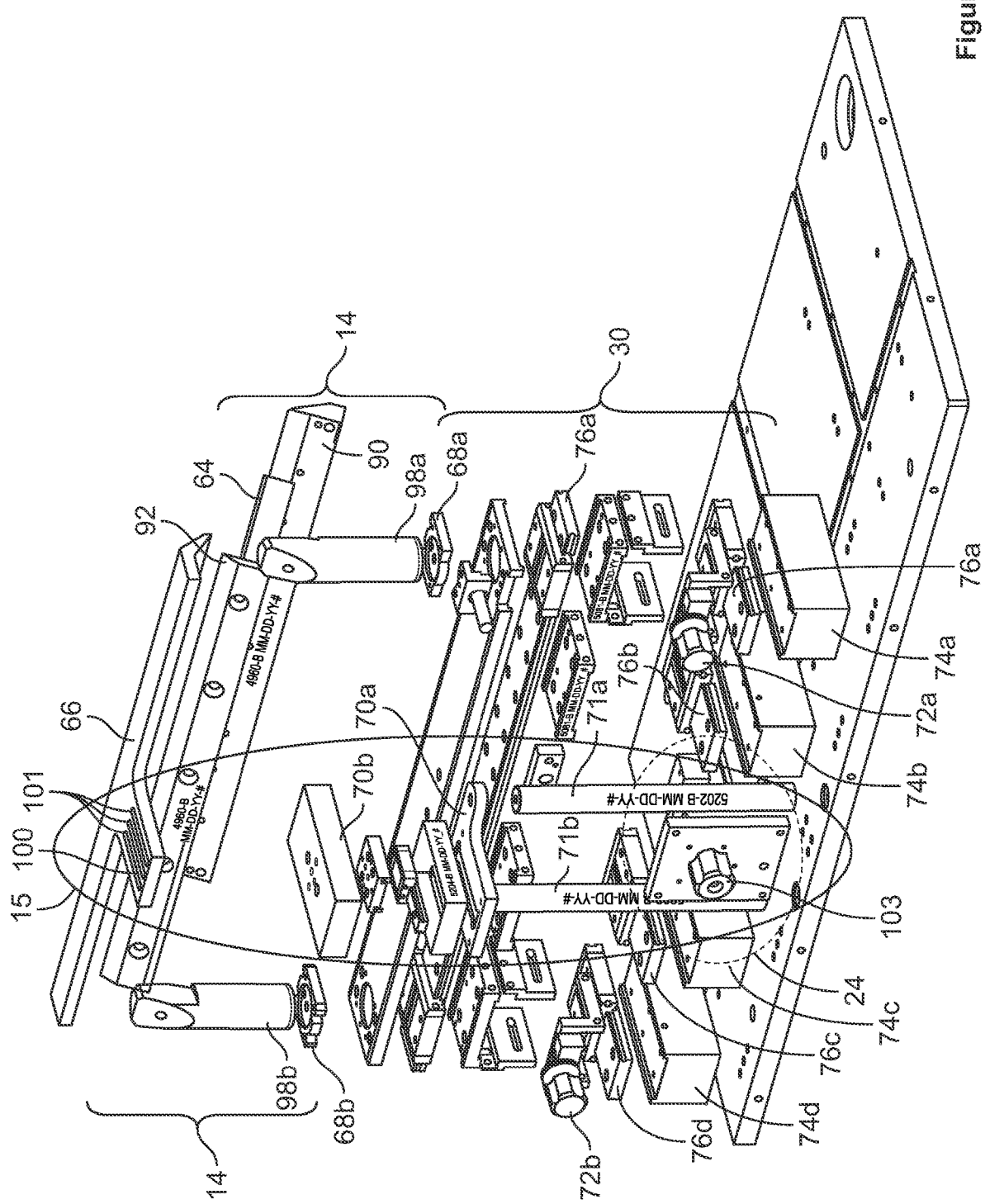
FIG. 16 is an exploded front elevational perspective view of the components shown in FIG. 15.

With reference briefly to FIGS. 15 and 16, the blade assembly 14 includes a blade 64 fastened between a blade holder 90 and a blade clamp 92 (see FIG. 16) all of which are longitudinally aligned with and proximate to the exterior surface 32 of the drum 20. Furthermore, when the blade 64 (and its associated holder 90 and clamp 92) is operably engaged with and/or fastened to the thickness adjustment mechanism 24 for movement in the direction shown by the arrow TA in FIG. 15, and also with the lateral movement mechanism 30 for movement in the direction shown by the arrow LM in FIG. 15. A gage knob 103 is provided among the components of the thickness adjustment mechanism 24 for manually moving the operably engaged blade 64 closer to, or farther from, the drum 20 and its external surface 32 (see the direction shown by the arrow TA in FIG. 15). Additionally, the lateral drive assembly 28 is operably engaged with both the blade motor assembly 26 and the lateral movement mechanism 30 for causing automated, controlled lateral reciprocating movement by the blade 64 in the direction shown by the arrow LM in FIG. 15. Some details of the lateral drive assembly 28 are visible within dash-dot lines defining area B in FIG. 3, which is enlarged in FIG. 19 and is discussed in further detail below.

Operation of the tissue separating device 10 involves lateral reciprocating movement of the blade 64 and rotation of the drum 20 which brings a planar tissue sample mounted on the exterior surface 32 of the drum 20 in continuous contact with the blade 64 which continuously cuts the planar tissue sample and produces a piece of tissue (not shown per se) and a portion of the tissue sample which remains mounted on the exterior surface 32 of the drum 20. Concurrently, the tissue pusher 66 pushes the piece of tissue (not shown) against the exterior surface 32 of the drum 20. Accordingly, controlled and precise positioning of the blade assembly 14, as well as the pusher assembly 15, proximate to the exterior surface 32 of the drum 20 is important.

Figure 10:
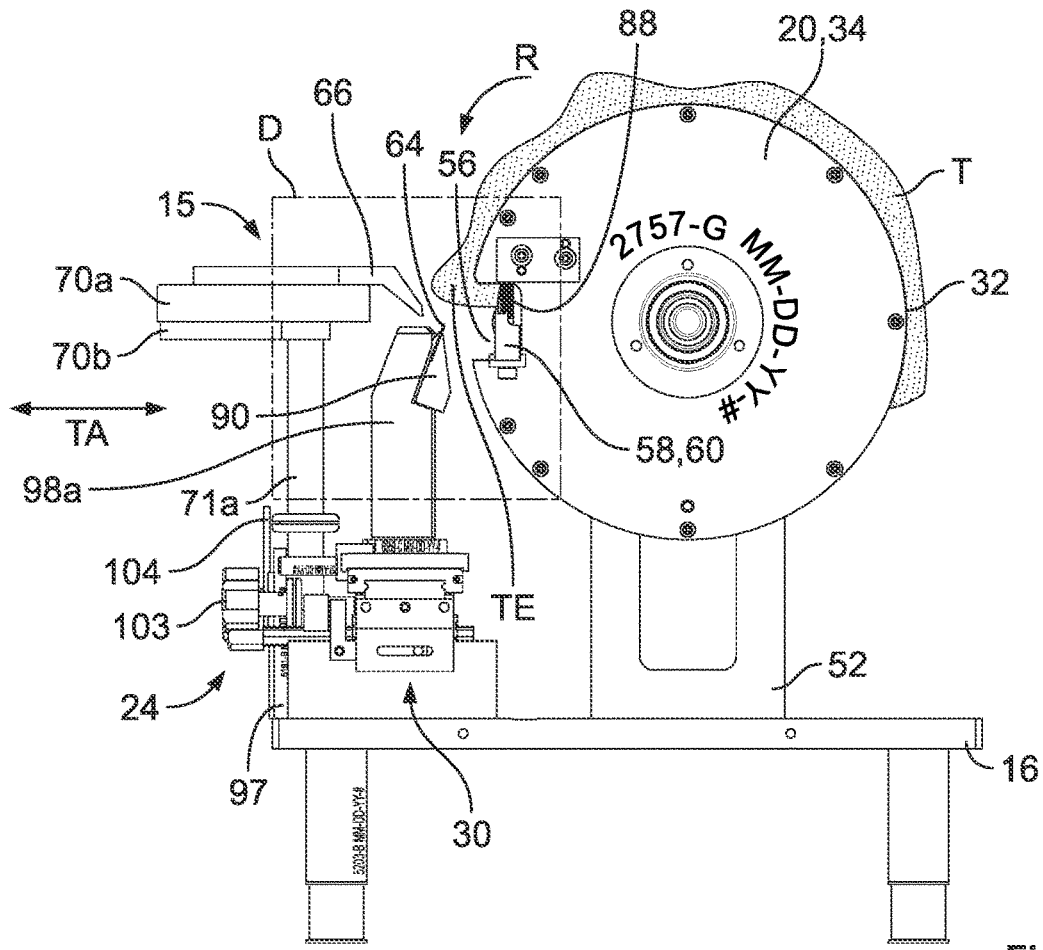
FIG. 10 is a right side elevational view of the device of FIG. 1, without the housing and motor assemblies to provide an unobstructed view of a tissue sample mounted on the drum and the relative positions of the blade assembly, tissue pusher assembly, drum assembly, and tissue sample.
Figure 11A:
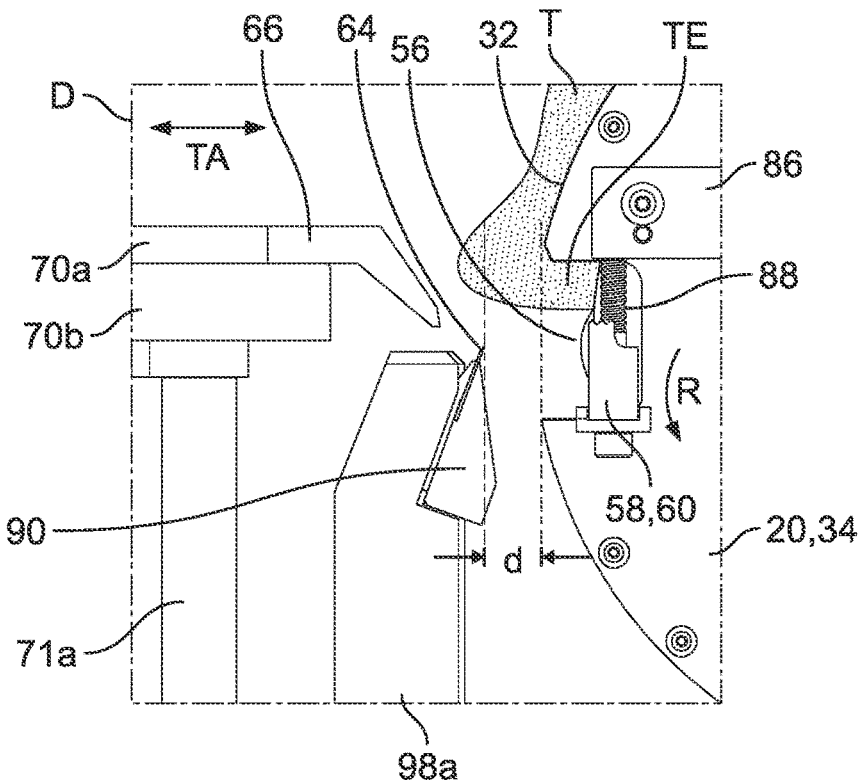
FIG. 11A is an enlarged view of the components shown in area D in FIG. 10, bounded by dash-dot lines, providing a detailed view of the blade and the tissue pusher as they are positioned relative to the groove of the drum and a mounted tissue sample.
Figure 11B:
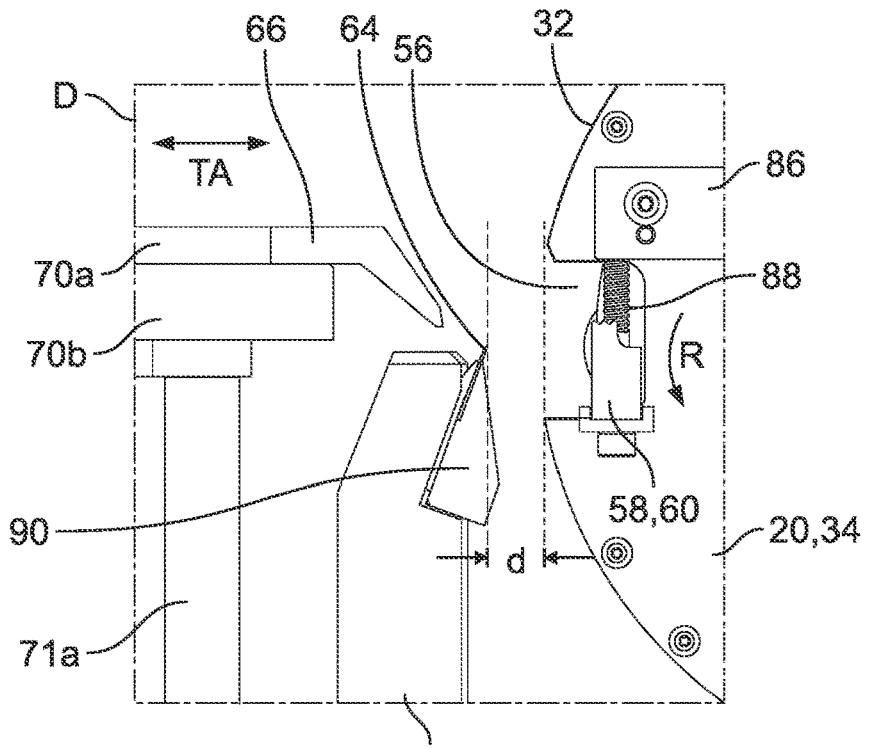
FIG. 11B is the enlarged view of FIG. 11A, but without the tissue sample to facilitate understanding of the relative positions of the components shown therein.

Turning now to FIGS. 10, 11A and 11B, the orientation and relative movement of the components which actually perform the cutting and separation of a tissue sample T to produce a planar tissue form useful as a graft will be described in further detail. More particularly, FIG. 10 provides a right side elevational view of the tissue separation device of FIG. 1, but without the housing 18 and motor assemblies 22, 26 to provide an unobstructed view of a tissue sample T mounted on the external surface 32 of the drum 20, as well as the relative positions of the drum 20, blade assembly 14, pusher assembly 15 and tissue sample T.

The area D in FIG. 10 which is bounded by dash-dot lines is enlarged in each of FIGS. 11A and 11B. FIG. 11A provides a detailed view of the blade 64 of the blade assembly 14 and the tissue pusher 66 of the pusher assembly 15 positioned relative to the drum 20 and its groove 56 and to the planar tissue sample T mounted on the exterior surface 32 of the drum 20 which is to be cut and separated. FIG. 11B is the same as in FIG. 11A except that there is no tissue sample T mounted on the drum 20. More particularly, the blade 64 is spaced apart from the exterior surface 32 of the drum 20 by a lateral (horizontal) distance d (see FIGS. 11A and 11B).

Figure 12:
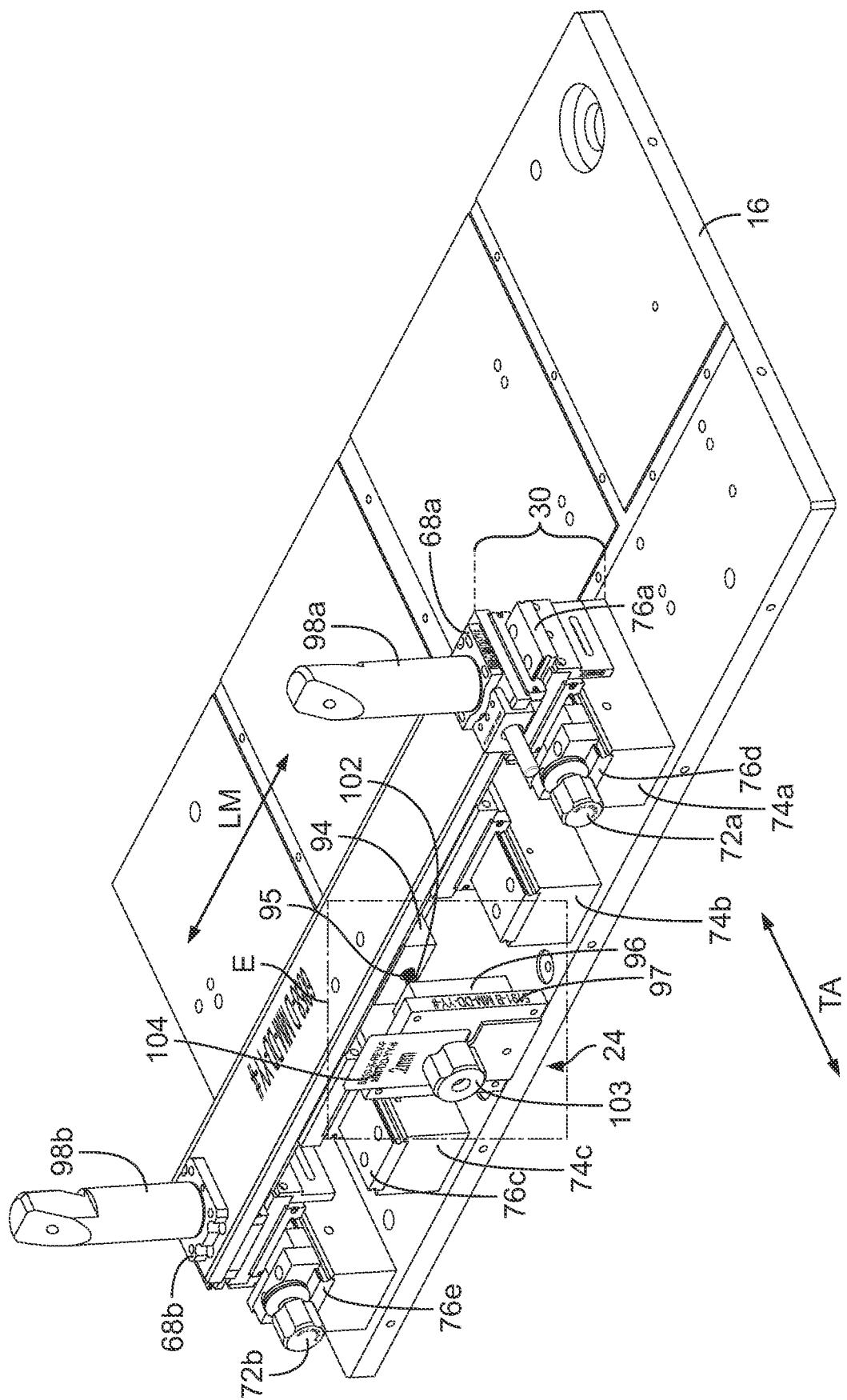
FIG. 12 is a front elevational perspective view of the thickness adjustment mechanism and the lateral movement mechanism, as mounted on the support base.
Figure 13:
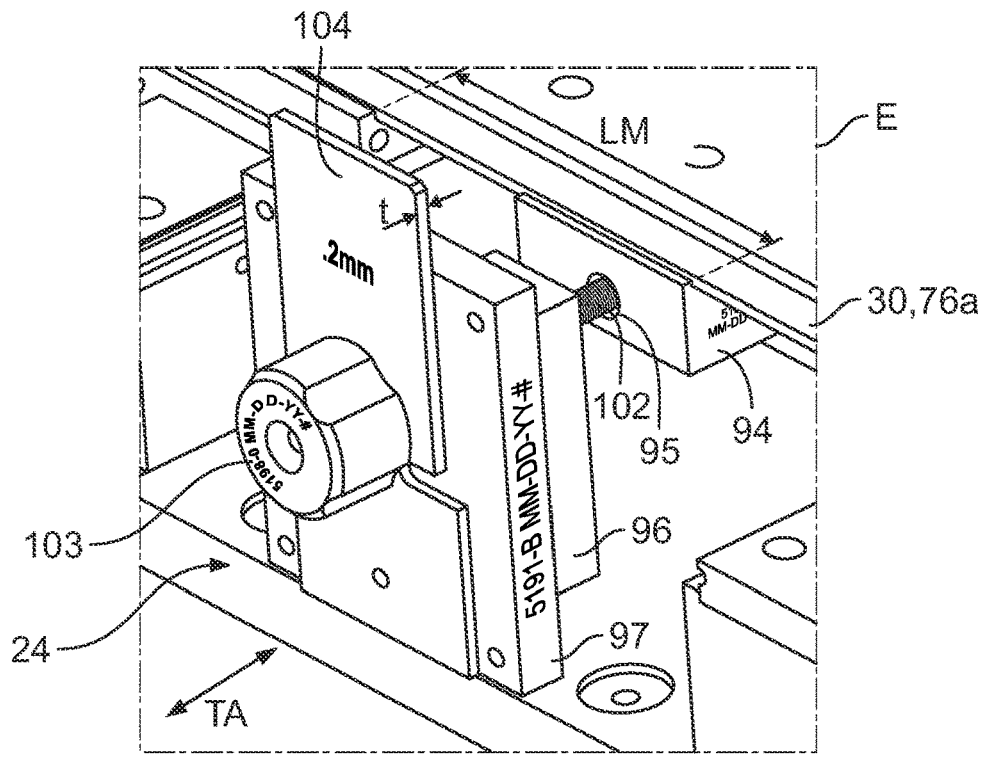
FIG. 13 is a is an enlarged view of the components shown in area E in FIG. 12, bounded by dash-dot lines, which provides a detailed view of the thickness adjustment mechanism.
Figure 14:
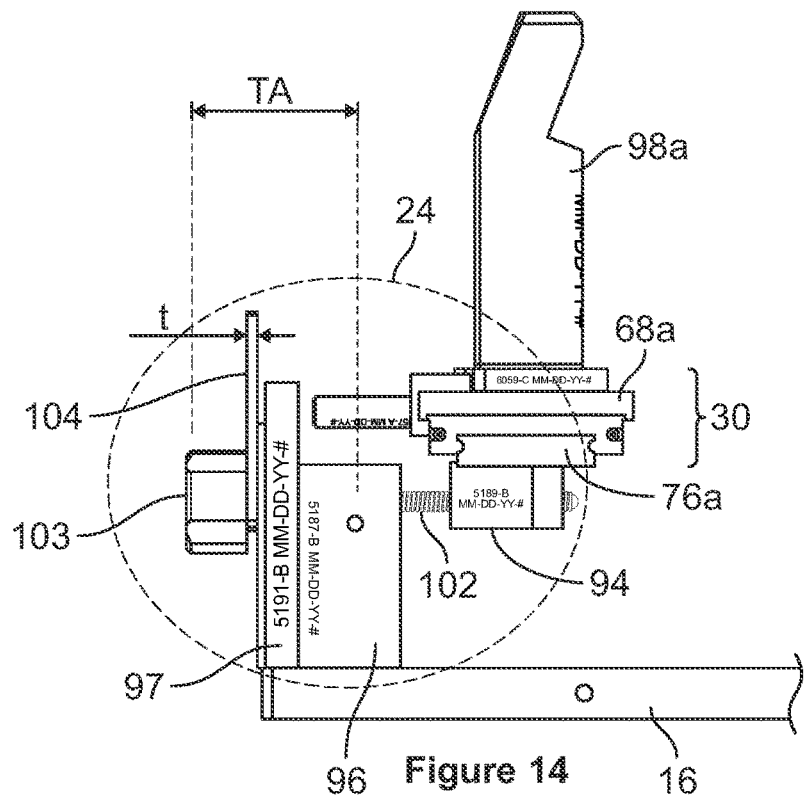
FIG. 14 is a right side elevational view of the thickness adjustment mechanism and the lateral movement mechanism of FIG. 12.

Looking now at FIGS. 12-14, the components and operation of the thickness adjustment mechanism 24, which enable precise, consistent movement of the blade assembly 14 and blade 64 (not shown, but see FIGS. 10, 11a, and 11b) to predetermined distances from the surface 32 of the drum 20 and, therefore also from a tissue sample mounted thereon, will now be described. More particularly, FIG. 12 shows the thickness adjustment mechanism 24, as well as the lateral movement mechanism 30, mounted on the support base 16, for moving the blade assembly 14 (not shown, but see FIG. 10) in the directions shown by the arrows TA, LM, respectively. Note that the drum assembly 12, blade assembly 14 and tissue pusher assembly 15 have been omitted from FIG. 12 to facilitate understanding of the remaining components. FIG. 13 is an enlarged view of area E of FIG. 12 and provides a clearer, more detailed view of the components of the thickness adjustment mechanism 24 and their arrangement. FIG. 14 is a right side view of the components shown in FIG. 12, and also provides a clearer view of the components thereof and their arrangement and orientation with one another and the lateral movement mechanism 30.

The thickness adjustment mechanism 24 enables manual movement of the blade assembly 14 closer to or further from the drum 20, which is how the distance d between the blade 64 and tissue sample T mounted on the surface 32 of the drum 20 is controlled and set prior to operation of the drum 20 and lateral movement mechanism 30 (not shown, but see FIGS. 10, 11a and 11b). As described below and shown in FIGS. 15-18, the lateral movement mechanism 30 rests on several guide rails 76a, 76b, 76c, 76d, 76e which permit limited linear movement of the lateral movement mechanism 30 and blade assembly 14 carried thereon in the directions indicated by arrow TA, i.e., closer and farther from the drum 20. With now reference particularly to FIGS. 13 and 14, a block 94 having a threaded bore 95 therethrough is affixed to the underside of the lateral movement mechanism 30. A bearing block 96 and adjacent seal plate 97 are securely mounted to the support base 16 and have aligned boreholes therethrough (not shown per se). A threaded shaft 102 having a knob 103 at one end is received through and supported in the aligned boreholes of the bearing block 96 and seal plate 97 and is also threadedly received through and engaged with the threaded bore 95 of the block 94 affixed to the lateral movement mechanism 30. In the foregoing arrangement, manually turning the knob 103 causes the block 94, with the lateral movement mechanism 30 and blade assembly 14 thereon, to move in the direction indicated by the arrow TA, i.e., closer to or further from the drum 20.

In addition, since the thickness adjustment mechanism 24 is manually operated, a thickness setting plate 104 having thickness t may be provided and positioned between the knob 103 and seal plate 97 which, in turn, enables an operator to adjust the distance d between the blade 64 and the exterior surface 32 of the drum 20 in a consistent manner. Positioning the thickness setting plate 104 in this manner facilitates and increases the precision with which the thickness adjustment mechanism 24 can be operated to position the blade 64. This arrangement of components provides a means of consistently and reproducibly setting distance d (see FIGS. 11A and 11B) between the blade 64 and the surface 32 of the drum 30, which will enable the reliable and reproducible cutting of a tissue sample T on the drum 20 to a thickness equal to about distance d.

Furthermore, a plurality of thickness setting plates 104 (not shown per se) may be made and available, each having a different thickness t which correlate as to a particular distance d and, consequently, to a particular desired tissue thickness. Each such setting plate 104 may have an alpha-numeric label to inform an operator of the distance d that will be created when that setting plate 104 is positioned between the knob 103 and seal plate 97 of the thickness adjustment mechanism 24 and the knob 103 is turned until flush and pressing securely against the thickness setting plate 104 and seal plate 97. For example, without limitation, a particular thickness setting plate 104 having a thickness t which provides a distance d of 0.2 millimeter (mm) may have a label such as "0.2 mm," as shown in FIG. 13.

Although the thickness t of each such setting plate 104 is generally not equal to the distance d produced by use of that setting plate 104 with the thickness adjustment mechanism 24, the thicknesses t of the setting plates 104 will be proportional to the distance d so that a setting plate 104 with a greater thickness t will produce a greater distance d and, conversely, a setting plate 104 with a smaller thickness t will produce a smaller distance d. Moreover, as will be understood by persons of ordinary skill in the relevant art, the thickness t required for a particular setting plate 104 to produce a particular distance d between the blade 64 and the drum 20, will depend somewhat on the particular device 10 with which it will be used and, therefore, the thickness t will generally be determined and calibrated empirically for each setting plate 104 based on the device 10 with which they will be used.

The plurality of thickness setting plates 104, each of which has a different thickness t for producing a specific desired distance d, provides a selection of various possible distances d and, consequently, a selection of various possible thicknesses for the piece of tissue that can be cut and separated from a planar tissue sample T. For example, without limitation, to produce a piece of tissue having thickness of about 1.8 mm from a tissue sample T, a previously manufactured and calibrated thickness setting plate 104 with a label of "1.8 mm" thereon would be selected and placed between the knob 103 and seal plate 97, and then the knob 103 turned until flush and pressing securely against the thickness setting plate 104 and seal plate 97. Similarly, for example without limitation, to produce both a 0.8 mm thick piece of tissue and a 0.2 mm thick piece of tissue from a single tissue sample T, a thickness setting plate 104 with a label of "1.0 mm" would be used to make a first cut into the tissue sample T, followed by use of a thickness setting plate 104 with a label of "0.2 mm" to make a second cut into the tissue sample T which remains mounted on the drum 20 after completion of the first cut. In another embodiment, for example without limitation, to produce a 0.4 mm thick piece of tissue from a tissue sample T, a thickness setting plate 104 with a label of "0.6 mm" would be used to make a first cut into the tissue sample T, followed by using a thickness setting plate 104 with a label of "0.2 mm" to make a second cut into the tissue sample T remaining mounted on the drum 20 after completion of the first cut.

As will be understood and determinable by persons of ordinary skill in the relevant art, the thickness of a piece of tissue that is cut from the tissue sample T will be approximately equal to (i.e., +/−about 0.05 mm) the spacing d between the blade 64 and the exterior surface 32 of the drum 20. Thus, the possible thickness of any piece of tissue that may be cut and separated from the planar tissue sample T will depend not only on the distance d between the blade 64 and the exterior surface 32 of the drum 20, but also on the initial thickness of the planar tissue sample T undergoing processing using the device 10 and other desired characteristics for the planar tissue graft that is to be produced.

Figure 17:
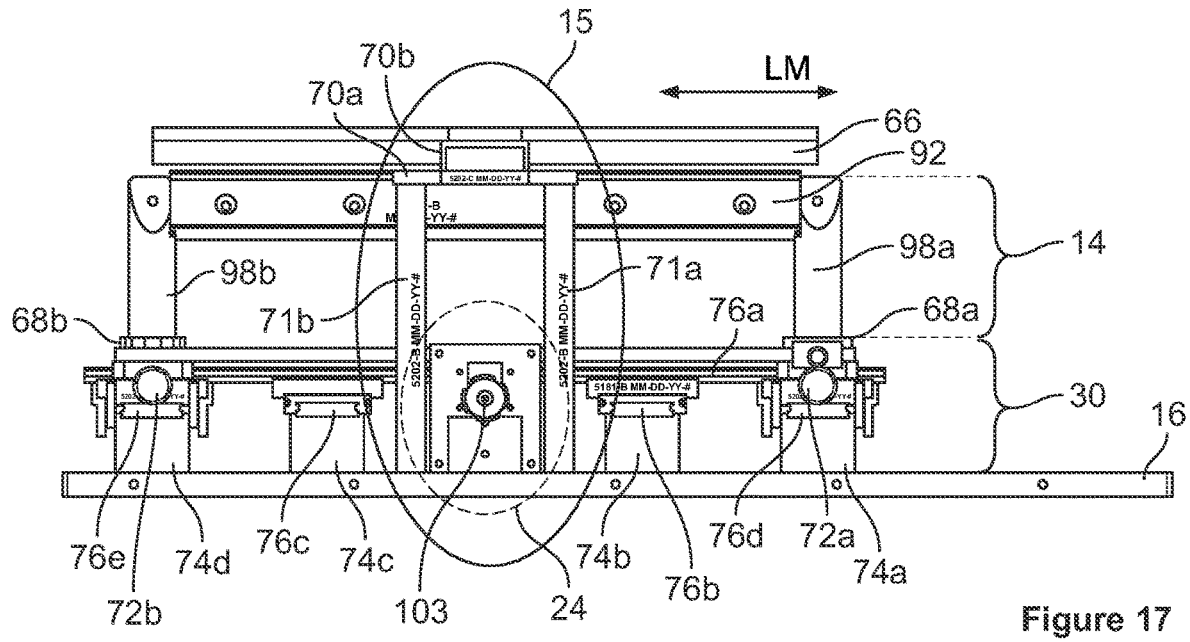
FIG. 17 is a front plan view of the components shown in FIG. 15, i.e., the blade assembly and its lateral movement and thickness adjustment mechanisms, as well as the tissue pusher assembly, all mounted on the support base.
Figure 18:
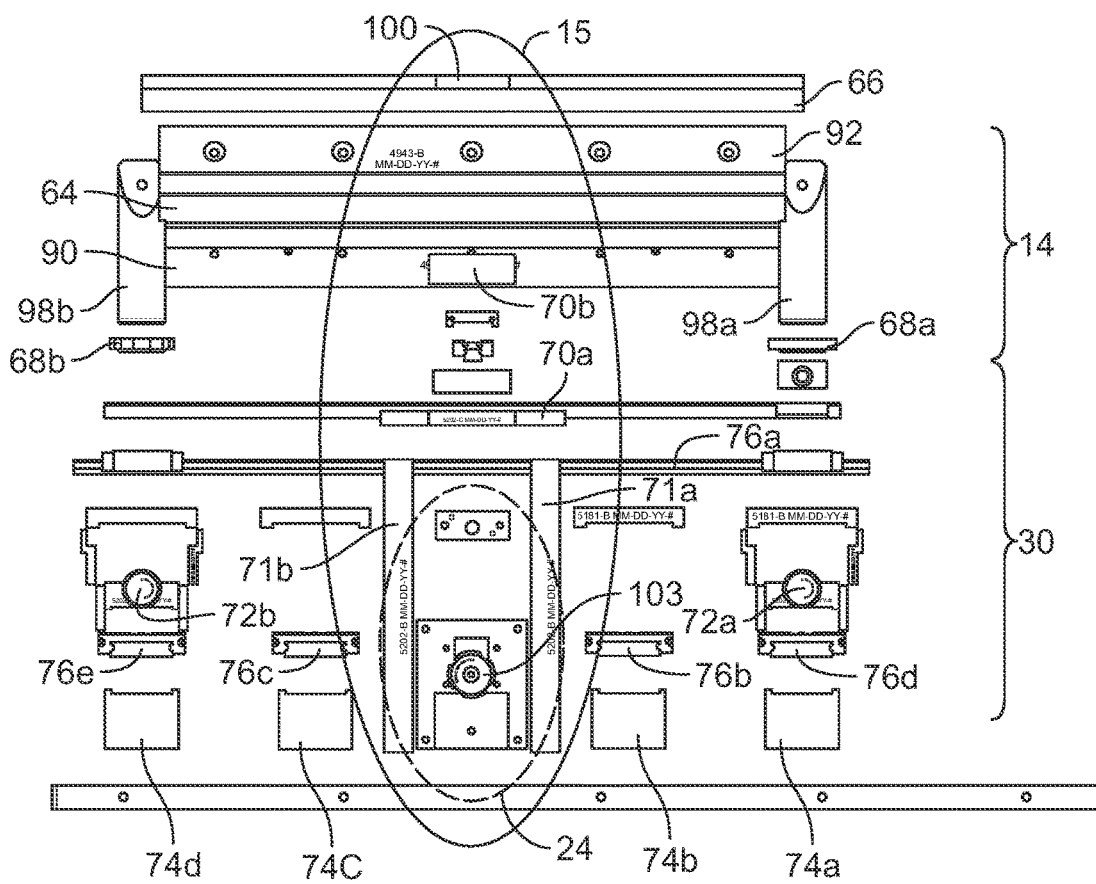
FIG. 18 is an exploded front plan view of the components shown in FIG. 17.
Figure 19:
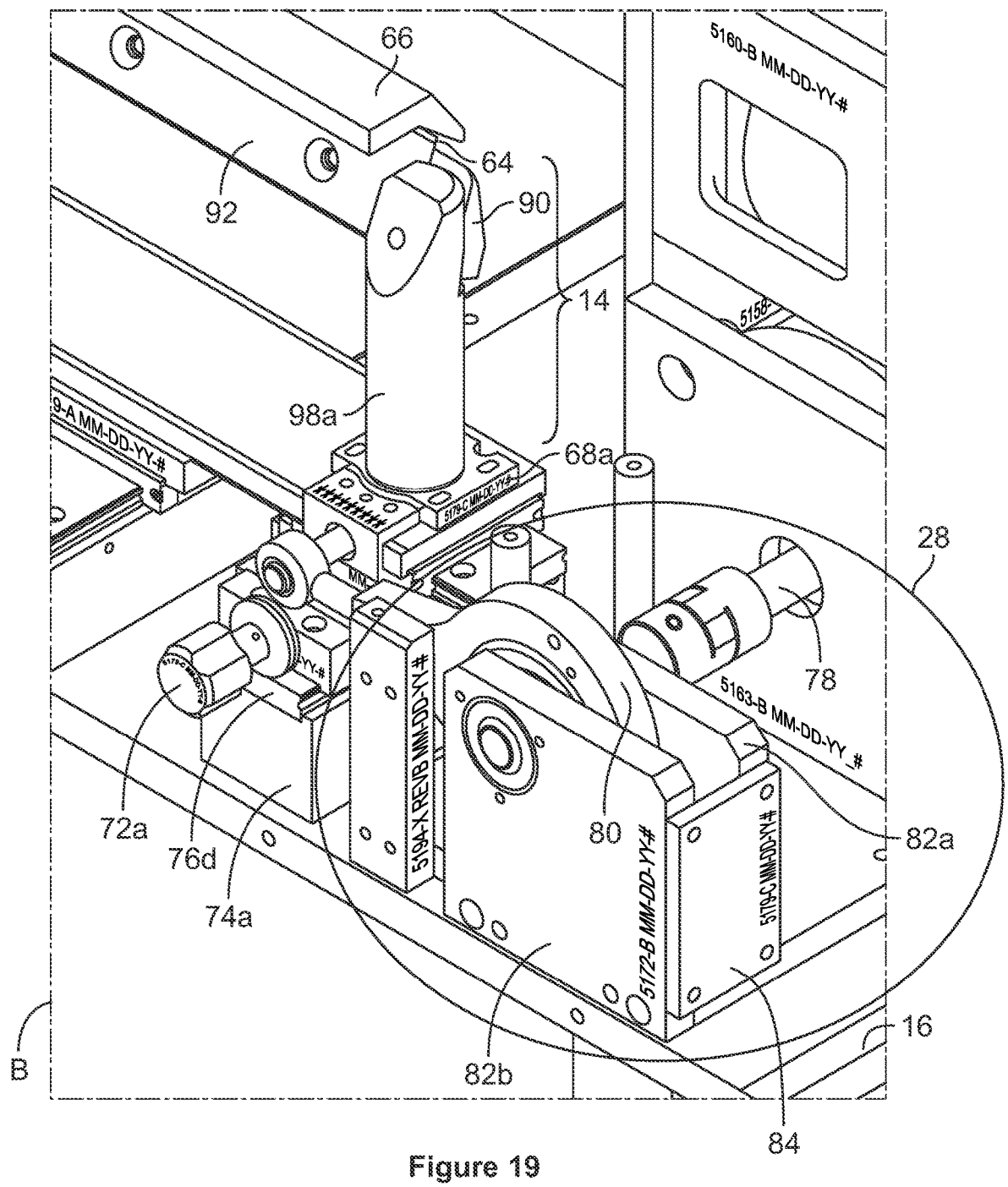
FIG. 19 is an enlarged view of the components shown in area B in FIG. 3, bounded by dash-dot lines, providing a detailed view of the drive assembly which couples the lateral movement mechanism with the blade motor assembly.

In each of FIGS. 4, 7, 8B and 9-11B, the tissue clamp 58 is shown in its closed position in the longitudinally oriented groove 56 of the drum 20. In each of FIGS. 10 and 11A, the edge TE of the tissue sample T has been inserted into the groove 56 of the drum 20 and retained there by the tissue clamp 58. Thus, when the drum 20 is rotated in the direction indicated by the arrow R, the tissue sample T is moved and continuously in contact with the blade 64, whereby the tissue sample T is continuously cut, creating a piece of tissue (not shown per se). Additionally, as the drum 20 rotates with the tissue T thereon, the tissue pusher 66 presses and thereby holds the tissue sample T against the exterior surface 32 of the drum 20 so that it is reliably, accurately and continuously cut by the blade 64. In some embodiments, the portion of the tissue sample T remaining on the drum 20 (not shown per se) may be further cut and separated after adjusting the distance d using the thickness adjustment mechanism 24 to bring the blade assembly 14 closer to the drum 20 and remaining portion of the tissue sample T mounted thereon. Additionally, in some embodiments, more than one planar tissue form may be produced from applying the tissue separation device to a single tissue sample. FIGS. 15-18 provide more detailed assembled and exploded views of the blade assembly 14, the thickness adjustment mechanism 24, the lateral movement mechanism 30, as well as the pusher assembly 15 which includes the tissue pusher 66. Several operational components, i.e., the drum assembly 12, the drum motor and blade motor assemblies 22, 26 and the lateral drive assembly 28 are omitted from FIGS. 15-18 for simplicity. More particularly, FIG. 15 provides a front elevational perspective view of the blade assembly 14 and its thickness adjustment and lateral movement mechanisms 24, 30, as well as the pusher assembly 15, which are all mounted on the support base 16, while FIG. 16 provides an exploded front elevational perspective view of the same components. FIG. 17 provides a front plan view of the components shown in FIGS. 15 and 16, while FIG. 18 provides an exploded front plant view of the same components.

FIG. 16, in particular, provides the clearest view of the constituent elements of the blade assembly 14, including the blade 64 which is held between the blade holder 90 and the blade clamp 92. As shown in each of FIGS. 15-18, the blade 64 and its associated holder 90 and clamp 92 are attached to and supported in an elevated position above the support base 16 by a pair of shafts 98a, 98b. Furthermore, the blade 64 and its associated holder 90 and clamp 92 are assembled and operably engaged with and fastened to both the thickness adjustment mechanism 24 and the lateral movement mechanism 30 by the shafts 98a, 98b for movement in the direction shown by the arrows TA, LM in FIG. 15. As also shown in FIGS. 15-18, the tissue pusher 66 has a slotted extension 100 which is slidingly engaged with and fastened to first and second plates 70a, 70b which are mounted at a fixed elevation above the support base 16 on a pair of posts 71a, 71b. The threaded shafts (not shown) of knobs 106a, 106b are inserted through the slots 101 of the slotted extension 100 of the tissue pusher 66, and into threaded holes in the second plate 70b. Movement of the tissue pusher 66 is guided and limited by the shafts of the knobs 106a, 106b sliding along the slots 101 and when the knobs 106a, 106b are turned and tightened against the slotted extension 100, further movement of the tissue pusher 66 is halted. This arrangement permits movement of the tissue pusher 66 closer to and further from the drum 20 in the direction shown by the arrow TA in FIG. 15, as well as securing the tissue pusher 66 in a fixed position by turning the knobs 106a, 106b. In this manner, the positioning of the tissue pusher 66 is independent of the positioning and movement of the blade assembly 14.

In a manner that will be generally understood and practicable by persons of ordinary skill in the relevant art based the general knowledge possessed by such persons together with FIGS. 1-19 provided herewith, each of the thickness adjustment and lateral movement mechanisms 24, 30 comprises several components including, but not limited to, brackets 68a, 68b, plates 70a, 70b, locking knobs 72a, 72b, blocks 74a, 74b, 74c, 74d and guide rails 76a, 76b, 76c, 76d, 76e (see FIGS. 15-18). For example, the knob 103 is provided among the components of the thickness adjustment mechanism 24 for manually moving the thickness adjustment mechanism 24 and the operably engaged blade 64 closer to, or farther from, the drum 20 and its external surface 32 (see the direction shown by the arrow TA in FIG. 15). Additionally, the lateral drive assembly 28 which itself also comprises several components including a coupling hub 78, a yoke 80, bearing plates 82a, 82b, a bracket 84 (see FIGS. 3 and 19), ball bearings (not visible) and a cam shaft (not visible), is operably engaged with both the blade motor assembly 26 and the lateral movement mechanism 30 for causing automated, controlled lateral reciprocating movement to blade 64 (see the direction shown by the arrow LM in FIG. 15). Some details of the lateral drive assembly 28 are visible within dash-dot lines defining area B in FIG. 3, which is enlarged in FIG. 19.

With reference now to FIGS. 20-23 in some embodiments, the tissue separation device 10 may be placed on a wheeled cart 110 which has an electrical enclosure 112 for containing various typical electrical control and power components (see FIG. 22) for delivering power and controlling the operation of the device 10, as will be known and readily understood by persons of ordinary skill in the relevant art. A disconnect switch 114 which is in electric communication with the electrical control and power components may be included for providing a single point at which power to the device 10 can be shut off quickly. Additionally, a foot switch 116 may be included for an operator to control the power supply through the electrical and power components to the device 10.

Figure 20:
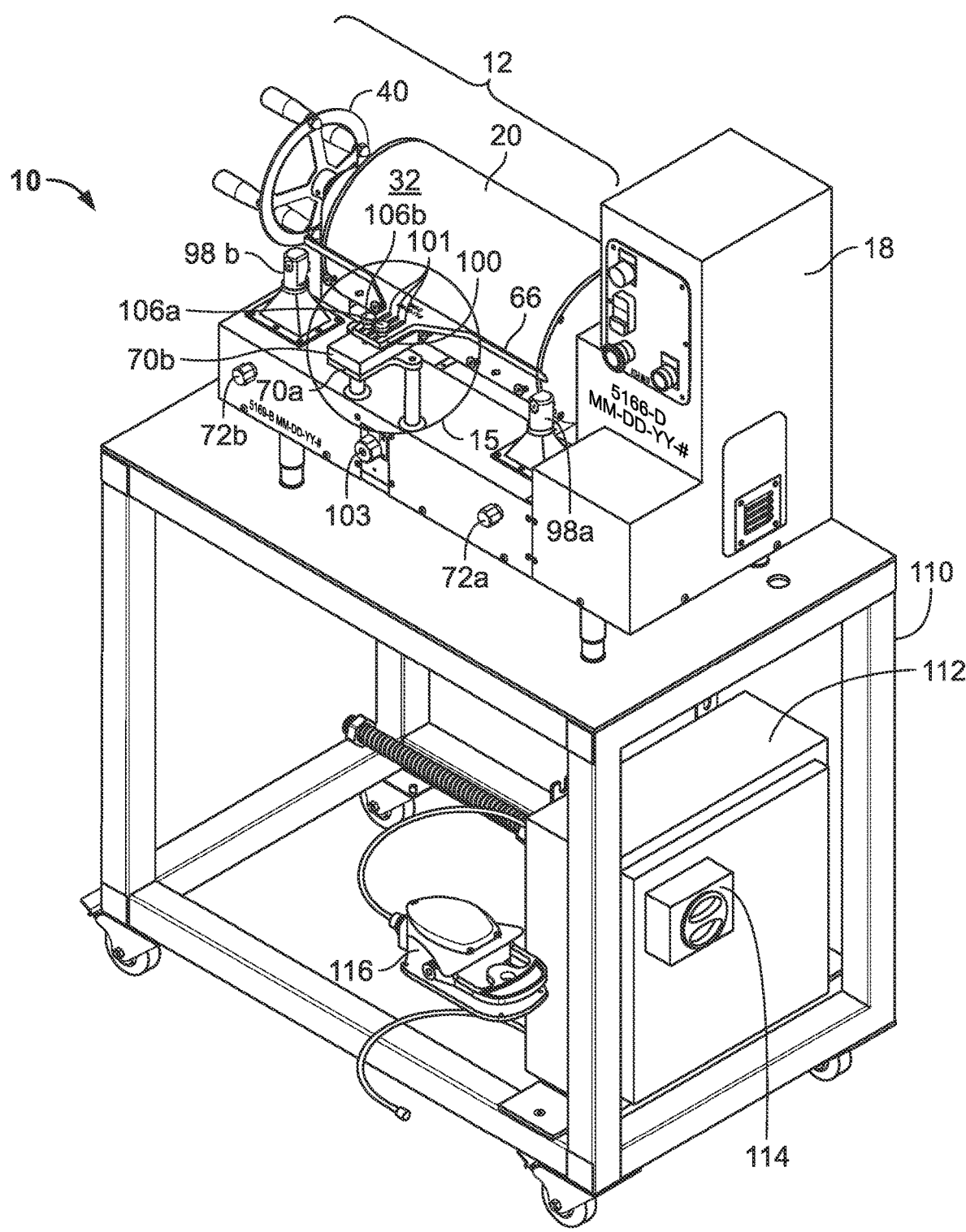
FIG. 20 is a front perspective view of the device of FIG. 1 mounted on a wheeled cart and having a control assembly mounted to the cart.
Figure 21:
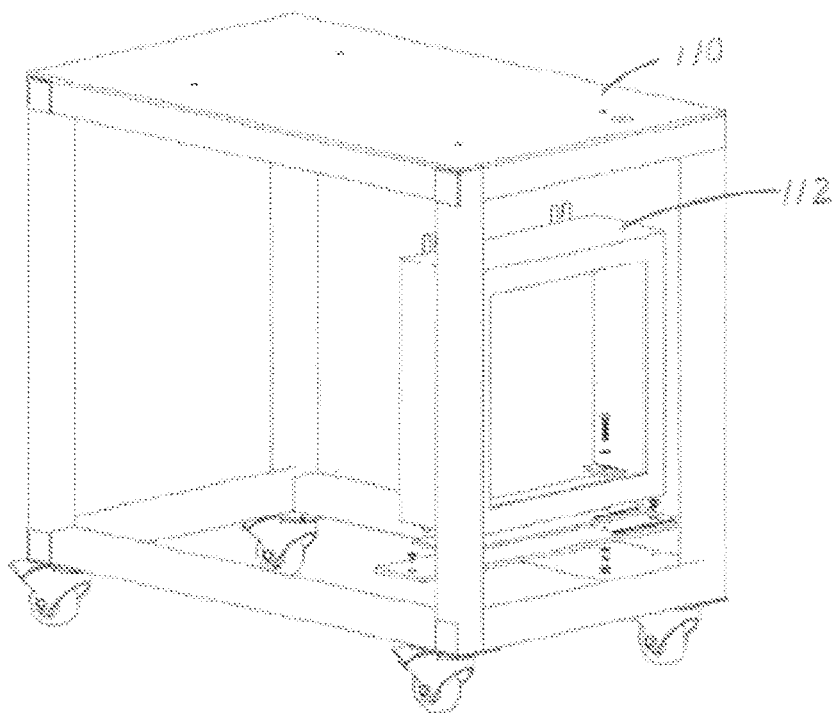
FIG. 21 is a front perspective view of the wheeled cart of FIG. 1 having only the electrical enclosure mounted thereon, without any control and power components.
Figure 22:
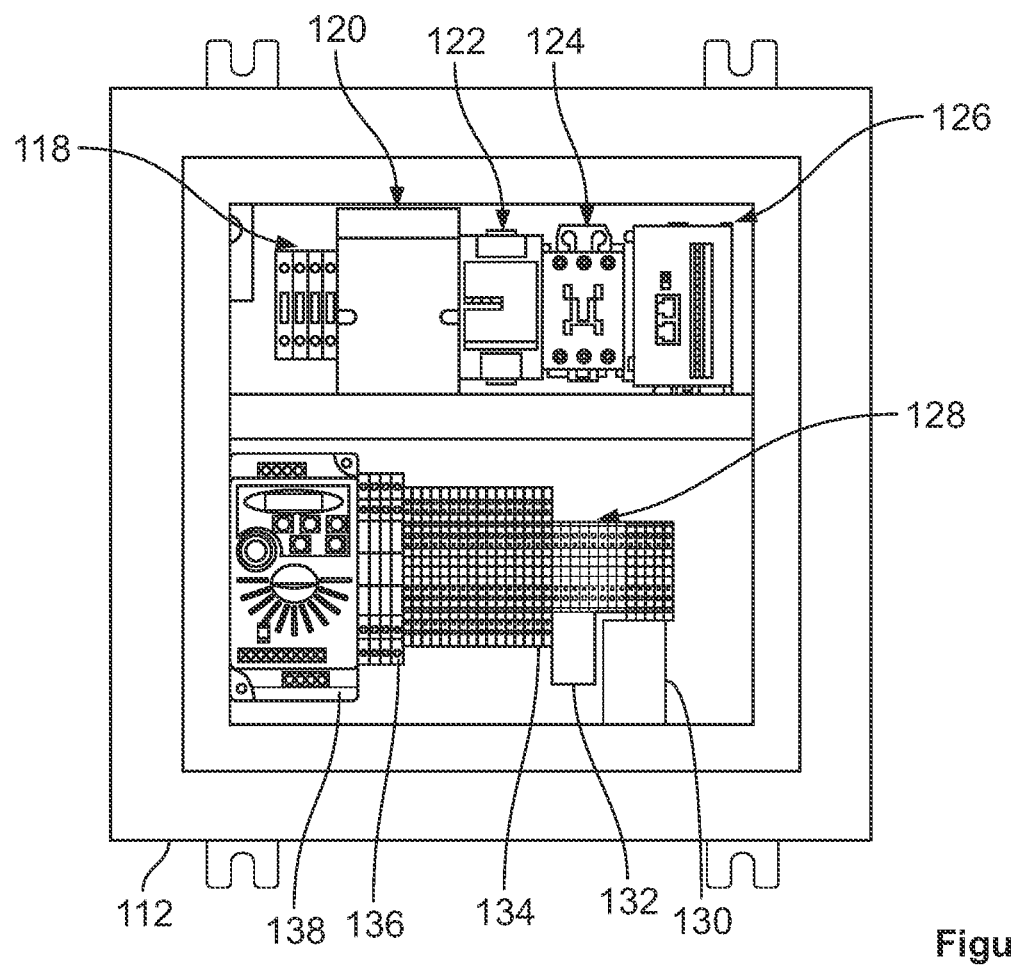
FIG. 22 is a front plan view of the control and power components of the control assembly as operatively installed in the electrical enclosure.
Figure 23:
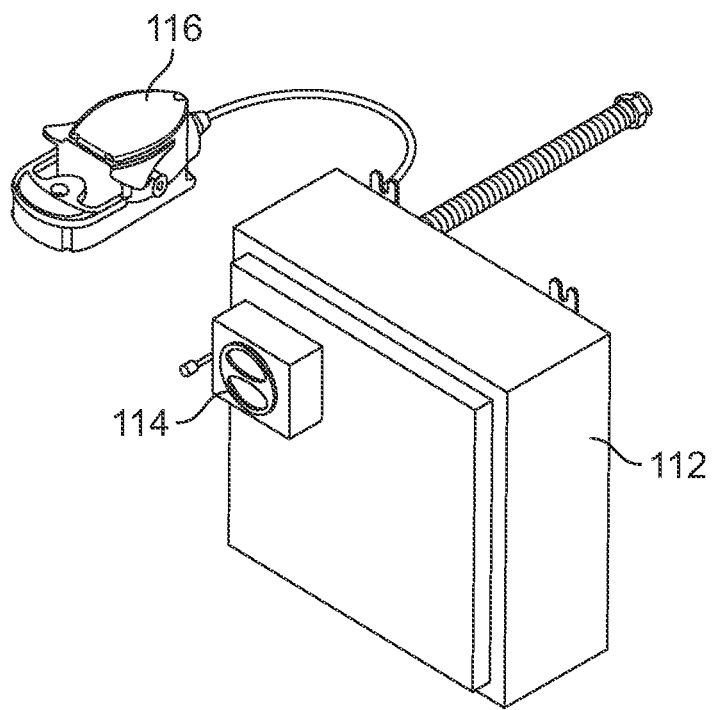
FIG. 23 is a perspective view of the control assembly showing the foot switch controller used by an operator to control rotation of the drum.

FIG. 22 provides a schematic front plan view of the electrical control and power components of the control assembly as operatively installed in the electrical enclosure. More particularly, in a manner that will be generally understood and practicable by persons of ordinary skill in the relevant art based the general knowledge possessed by such persons together with FIGS. 20 and 22 provided herewith, electrical control and power components may, for example, include: a fuse terminal 118, a single phase speed controller 120, a power supply (e.g., 24 V) 122, an IEC (International Electrotechnical Commission) contactor switch 124, a programmable logic controller (PLC) 126, a feed through terminal 128, a VDC power supply converter 130, a programming cable 132, a terminal block 134, a relay 136, and a variable frequency drive (VFD) controller 138 (see FIG. 22).

The configuration described above for the drum assembly 12, blade assembly 14 and pusher assembly 15, allows a generally planar tissue sample to be cut and separated to produce a planar tissue form suitable for use as a graft. More particularly, the drum 20 rotates controllably with a tissue sample affixed thereon by inserting an edge TE of the tissue sample T into a groove 56 on the drum 20 and retaining the edge TE in the groove 56 with the pivotable tissue clamp 58. As the drum 20 and tissue sample T rotate toward a laterally reciprocating blade 64 which is longitudinally aligned with the drum 20, the leading edge of the tissue sample T is continuously contacted with the blade 64 and, thereby, is continuously cut in a controlled manner to produce a planar tissue form having a precise and consistent predetermined maximum thickness. Additionally, the tissue pusher 66 of the pusher assembly 15 is also longitudinally aligned with the rotating drum 20 and tissue sample T mounted thereon and continuously separates the piece of tissue being cut from the tissue sample T. The tissue sample may be processed using the tissue separation device 10 before, during or after any one or more other physical and chemical processing techniques.

Operation of the tissue separation device 10 to cut a dermis tissue sample T will now be explained in detail as an exemplary embodiment of a method for using the device. It should be understood that although the following embodiment is described based on cutting a dermis tissue sample, other types of tissues as described earlier are also suitable for use to operate the device in accordance with the present method.

Initially, the device 10 should be thoroughly cleaned and checked for proper movement and power supply of all relevant components. In particular, the blade 64, tissue pusher 66 are cleaned and sterilized and external surface 32 of the drum 20 is cleaned and disinfected prior to commencement of mounting and cutting each new tissue sample. The cleaned, sterilized blade 64 is assembled with its holder 90 and clamp 92 and affixed to the shafts 98a, 98b. The cleaned and sterilized tissue pusher 66 is assembled with the plates 70a, 70b of the pusher assembly 15 using the knobs 106a, 106b in the slots 101 in the extension 100 of the pusher 66.

The tissue sample T should be prepared and ready for cutting prior to cleaning and assembly of the tissue separation device 10. As will be recognized and understood by persons of ordinary skill in the relevant art, such preparation may include, without limitation, one or more of the following: isolation of the tissue sample by removal of debris, unwanted tissue, blood, etc., cutting or other size modification or reduction techniques, chemical or physical decellularizing, chemical or physical delipidizing, chemical or other disinfection, sterilization by chemical or irradiation or other technique, pH adjustment, combination with preservatives, endogenous or exogenous cells, growth factors, antibiotics, or other substances, hydration by combining with water, saline, or other fluid. Any one or more such processing steps may also be performed after cutting using the tissue separation device 10. In an exemplary embodiment, dermis tissue has been cut to an approximate rectangular shape with a width (W) of less than about 40 cm and a length of less than, for example without limitation, about 68 cm, such as less than about 60 cm, or less than about 50 cm, or even less than about 40 cm.

The desired thickness of the cut tissue piece(s) to be formed using the device 10 must be decided, and this will, in turn, determine the particular thickness setting plate 104 to be selected and positioned on the thickness adjustment mechanism 24 as described above (i.e., between the knob 103 and the seal plate 97). This will, in turn, set the distance d setting between the blade 64 of the blade assembly 14 and the exterior surface 32 of the drum 20. For example, without limitation, where the initial planar tissue sample T has an average thickness of 2.2 mm and a minimum thickness of about 2.0 mm, and it is desired to prepare two pieces of tissue for use as grafts, where one piece is about 0.8 mm thick and the other is about 0.2 mm thick, first a thickness setting plate 104 having a thickness which provides a distance d of 1.0 mm (e.g., a setting plate 104 which has been manufactured and inspected to a high degree of accuracy (per drawing specifications) and has a label of "1.0 mm") would be used to make a first cut, followed by use of a second thickness setting plate 104 having a thickness which provides a distance d of 0.2 mm (e.g., a setting plate 104 which has been calibrated and has a label of "0.2 mm") would be used to make second cut, resulting in a first piece of tissue having thickness of about 0.8 mm being cut and separated, leaving a second piece of tissue (not shown) on the drum 20 having a thickness of about 0.2 mm. In every case, the planar tissue sample should be approximately the width W and length (i.e., less than the total circumference of the exterior surface 32 of the drum 20) of the drum 20 and should be cut prior to mounting on the drum 20 if necessary.

Next the tissue clamp 58 is moved to its open position (see FIG. 8A) and the dermis tissue sample T is laid flat and evenly over the external surface 32 of the drum 20, with the epidermis layer in contact with the surface 32 of the drum 12 and one of its <40 cm edges aligned with and extending across the groove 56 of the drum 20. The tissue clamp 58 is moved to its closed position (see FIG. 8B) and fastened in place. The knob 103 is adjusted until the blade 64 is a desired distance d from the drum 20 which is sufficient to cut and separate any adipose tissue from the dermis tissue sample T. The drum 20 is manually turned using the hand wheel 40 until the blade 64 is proximate to the tissue clamp 58 and groove 56, then turn on power to the device 10 and allow the drum 20 to rotate and the blade 64 to reciprocate until the entire dermis tissue sample T has passed by the blade. A second pass may be necessary to remove all adipose tissue from the sample T.

After removal of the adipose, the dermis tissue sample T remains on the drum 20 and the hand wheel 40 is again used to position the groove 58 and leading edge of tissue TE to be aligned with the blade 64. A thickness setting plate 104 which will provide a distance d of 1.0 mm between the blade 64 and the drum 20 (e.g., having a label of "1.0 mm") is positioned onto the thickness adjustment mechanism 24 as described above, and the knobs 72a and 72b are used to secure the blade 64 in place at a distance (d) of 1.0 mm from the drum 20. The tissue pusher 66 is positioned at the desired distance from the drum 20, where the desired distance will be slightly greater (see, e.g., FIGS. 11A and 11B) than the distance d which has been selected for the desired thickness of the cut tissue product to be formed using the device 10. Cutting is commenced by manual rotation of the drum 20, following by turning on the power and allowing the drum 20 to rotate and the blade 64 to reciprocate until the entire dermis tissue sample T has passed by the blade, thereby producing a first piece of tissue separated from the remaining portion of the tissue sample T which remains on the drum 20 and which is about 1.0 mm thick. The resulting separated first piece of tissue of is typically discarded.

Next a thickness setting plate 104 providing a distance d of 0.2 mm (e.g., having a label of "0.2 mm") is installed onto the thickness adjustment mechanism 24 as described above, using knobs 72a, 72b to secure the blade 64 in place at a distance d of 0.2 mm from the drum 20. The tissue pusher 66 is positioned at the desired distance from the drum 20, which will be slightly greater (see, e.g., FIGS. 11A and 11B) than the distance d which has been selected for the desired thickness of the cut tissue product to be formed using the device. Cutting is commenced by manual rotation of the drum 20, following by turning on the power and allowing the drum 20 to rotate and the blade 64 to reciprocate until the entire dermis tissue sample T has passed by the blade. The resulting separated second piece of tissue has a thickness of about 0.8 mm and is collected and set aside for further processing as necessary. The piece of tissue sample which remains on the drum is about 0.2 mm thick. Further processing, as desired, may follow.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

We claim:

1. A device for producing a tissue product from a tissue sample,
    wherein the tissue product comprises a piece of tissue having a generally planar configuration and a predetermined maximum thickness between first and second surfaces thereof, the device comprising:
    (A) a support base (16) for supporting the device on a horizontal surface;
    (B) a drum assembly (12) mounted on the support base (16) and comprising:
        a rotatable cylindrical drum (20) having a longitudinal axis (LA) oriented parallel to the horizontal surface and an exterior cylindrical surface (32),
        a shaft (42) extending through the drum (20) coincident with the longitudinal axis (LA), and
        a hand wheel mounted to the drum (20) capable of manually rotating the drum (20);
    (C) a drum motor assembly (22) mounted to the support base (16) and operably engaged with the shaft (42) of the drum assembly (12) and capable of continuously rotating the drum (20) about the longitudinal axis (LA);
    (D) a blade assembly (14) comprising a blade (64) which is longitudinally aligned with and proximate to the exterior surface (32) of the drum (20) and capable of cutting a tissue sample mounted on the exterior surface (32) to form the tissue product;
    (E) a lateral movement mechanism (30) operably engaged with and carrying the blade assembly (14) and capable of moving the blade assembly (14) reciprocatingly in a lateral direction (LM);
    (F) a lateral drive assembly (28) operably engaged with and capable of operating the lateral movement mechanism (30) to move the blade assembly (14) reciprocatingly in a lateral direction (LM), wherein the lateral movement mechanism (30), the lateral drive assembly (28), and the blade assembly (14) are, together, capable of continuously cutting a tissue sample mounted on the exterior surface (32) of the drum (20) by reciprocatingly moving the blade assembly (14) and blade (64) thereof in the lateral direction (LM);
    (G) a blade motor assembly (26) mounted to the support base (16) and operably engaged with and capable of actuating the lateral drive assembly (28) to operate the lateral movement mechanism (30); and
    (H) a thickness adjustment mechanism (24) which is partially mounted on the support base (16) and partially mounted to the lateral movement mechanism (30), thereby being operably engaged with the blade assembly (14), wherein the thickness adjustment mechanism (24) is capable of setting the maximum predetermined thickness of the tissue product by moving the blade assembly (14) in a linear direction (TA), which is perpendicular to the longitudinal axis (LA) of the drum (20), and positioning the blade (64) a distance (d) from the exterior surface (32) of the drum (20), wherein the distance (d) is equal to the maximum predetermined thickness of the tissue product, wherein the thickness adjustment mechanism (24) comprises:
        a block (94) having a threaded bore (95) and being mounted to the lateral movement mechanism (30) which slidingly rests on two or more guide rails (76a, 76b) which enable movement of the lateral movement mechanism (30) and the blade assembly (14) carried thereon in the linear direction (TA);
        a bearing block (96) and adjacent seal plate (97) which are fixedly mounted to the support base (16) and have aligned threaded bores therethrough which are also aligned with the threaded bore (95) of the block (94); and
        a threaded shaft (102) having a knob (103) at one end thereof, wherein the threaded shaft (102) is threadedly received through and engaged with the threaded bores of each of the block (94), the bearing block 196) and the seal plate (97), and
    wherein the thickness adjustment mechanism (24) is manually operable by turning the knob (103) which moves the lateral movement mechanism (30) and the blade assembly (14) carried thereon in the linear direction (TA) and positions the blade (64) a distance (d) from the exterior surface (32) of the drum (20).

2. The device of claim 1, further comprising one or more thickness setting plates (104) for setting the distance (d) between the blade (64) of the blade assembly (14) and the exterior surface (32) of the drum (20), wherein each of the one or more thickness setting plates (104) has a different respective thickness (t) and, when a selected one of the thickness setting plates (104) is positioned between the knob (103) and the seal plate (97), and the knob (103), the selected one of the thickness setting plates (104), and the seal plate (97) are in contact with one another, the distance (d) between the blade (64) of the blade assembly (14) and the exterior surface (32) of the drum (20) is equal to the respective thickness (t) of the selected one of the setting plates (104).

3. A method for producing a tissue product from a tissue sample using the device of claim 2, wherein the tissue product comprises a piece of tissue having a generally planar configuration and a predetermined maximum thickness between first and second surfaces thereof, the method comprising the sequential steps of:
  (1) optionally, modifying the tissue sample to have a size and shape suitable for use with the device
  (2) mounting the tissue sample on the exterior surface (32) of the drum (20);
  (3) selecting and setting the maximum predetermined thickness of the tissue product, using the thickness adjustment mechanism (24) and a selected one of the one or more thickness setting plates (104), by selecting one of the one or more thickness setting plates (104), positioning the selected one thickness setting plate (104) between the knob (103) and the seal plate (97), turning the knob (103), until the knob (103), the selected one thickness setting plate (104), and the seal plate (97) are in contact with one another, thereby positioning the blade (64) of the blade assembly (14) a distance (d) from the exterior surface (32) of the drum (20), whereby the distance (d) between the blade (64) and the exterior surface (32) of the drum (20) is equal to the respective thickness (t) of the selected one thickness setting plate (104);
  (4) positioning the tissue sample in a suitable position relative to the blade (64) of the blade assembly (14) by manually rotating the drum (20) using the hand wheel, wherein the suitable position is when a leading edge of the tissue sample is proximate to but not yet in contact with the blade (64);
  (5) commencing lateral reciprocating movement of the blade assembly (14) by supplying power to the blade motor assembly (26), which actuates the lateral drive assembly (28), which operates the lateral movement mechanism (30), which moves the blade assembly (14) reciprocatingly in the lateral direction (LM);
  (6) commencing rotation of the drum (20) and the tissue sample mounted on the exterior surface (32) thereof by supplying power to the drum motor assembly (22);
  (7) allowing the concurrent reciprocating movement of the blade assembly (14) and rotation of the drum (20) and the tissue sample mounted on the exterior surface (32) thereof to continue until all of the tissue sample has passed by the blade assembly (14) to form a first tissue product which remains on the drum and a second piece of tissue which has been separated from the first tissue product;
  (8) optionally, removing the first tissue product from the drum (20), wherein the first tissue product has a generally planar configuration, a predetermined maximum thickness, and, optionally, consists essentially of a selected tissue type;
  (9) optionally, removing the first tissue product from the drum (20) and mounting the second piece of tissue to the exterior surface (32) of the drum (20) as a next tissue sample to be cut, and repeating steps (3) to (7); and
  (10) optionally, leaving the first tissue product on the drum (20) and using the first tissue product as a next tissue sample to be cut, and repeating steps (4) to (7).

4. The device of claim 1, wherein the thickness adjustment mechanism (24) further comprises at least one locking knob which is capable of locking the thickness adjustment mechanism (24) in place after positioning the blade (64) a desired distance (d) from the exterior surface (32) of the drum (20) by turning the knob (103) and moving the lateral movement mechanism (30) and the blade assembly (14) carried thereon.

5. The device of claim 1, wherein the rotatable cylindrical drum (20) has an adjustable rotational speed.

6. The device of claim 1, wherein the drum assembly (12) further comprises a tissue clamp (58) for holding the tissue sample in place on the exterior surface (32) of the drum (20), and the drum (20) further comprises a longitudinally oriented groove which is sized and shaped to receive the tissue clamp (58) and a portion of the tissue sample therein.

7. The device of claim 1, wherein the drum assembly (12) further comprises at least one upright bracket (52) mounted to the support base (16) and having an opening (54) for rotatably receiving an end (48) of the shaft (42) therein, thereby rotatably supporting the drum (20) above the support base (16).

8. The device of claim 1, further comprising a housing (18) which is sized and shaped to cover and conceal one or more of: (C) the drum motor assembly (22), and (G) the blade motor assembly (26).

9. A device for producing a tissue product from a tissue sample, wherein the tissue product comprises a piece of tissue having a generally planar configuration and a predetermined maximum thickness between first and second surfaces thereof, the device comprising:
  (A) a support base (16) for supporting the device on a horizontal surface;
  (B) a drum assembly (12) mounted on the support base (16) and comprising:
    a rotatable cylindrical drum (20) having a longitudinal axis (LA) oriented parallel to the horizontal surface and an exterior cylindrical surface (32),
    a shaft (42) extending through the drum (20) coincident with the longitudinal axis (LA), and
    a hand wheel mounted to the drum (20) capable of manually rotating the drum (20);
  (C) a drum motor assembly (22) mounted to the support base (16) and operably engaged with the shaft (42) of the drum assembly (12) and capable of continuously rotating the drum (20) about the longitudinal axis (LA);
  (D) a blade assembly (14) comprising a blade (64) which is longitudinally aligned with and proximate to the exterior surface (32) of the drum (20) and capable of cutting a tissue sample mounted on the exterior surface (32) to form the tissue product;
  (E) a lateral movement mechanism (30) operably engaged with and carrying the blade assembly (14) and capable of moving the blade assembly (14) reciprocatingly in a lateral direction (LM);
  (F) a lateral drive assembly (28) operably engaged with and capable of operating the lateral movement mechanism (30) to move the blade assembly (14) reciprocatingly in a lateral direction (LM), wherein the lateral movement mechanism (30), the lateral drive assembly (28), and the blade assembly (14) are, together, capable of continuously cutting a tissue sample mounted on the exterior surface (32) of the drum (20) by reciprocatingly moving the blade assembly (14) and blade (64) thereof in the lateral direction (LM);
  (G) a blade motor assembly (26) mounted to the support base (16) and operably engaged with and capable of actuating the lateral drive assembly (28) to operate the lateral movement mechanism (30);

(H) a thickness adjustment mechanism (24) which is partially mounted on the support base (16) and partially mounted to the lateral movement mechanism (30), thereby being operably engaged with the blade assembly (14), wherein the thickness adjustment mechanism (24) is capable of setting the maximum predetermined thickness of the tissue product by moving the blade assembly (14) in a linear direction (TA), which is perpendicular to the longitudinal axis (LA) of the drum (20), and positioning the blade (64) a distance (d) from the exterior surface (32) of the drum (20), wherein the distance (d) is equal to the maximum predetermined thickness of the tissue product; and (I) a tissue pusher assembly (15) comprising a tissue pusher (66) slidably mounted to the support base (16) and which is longitudinally aligned with and proximate to the exterior surface (32) of the drum (20), moveable in the same linear direction (TA) as, and independently of, the thickness adjustment mechanism (24), and capable of pressing and holding a tissue sample on the exterior surface (32) during operation of the device.

10. The device of claim 9, wherein the (I) tissue pusher assembly (15) further comprises
at least one post (71a, 71b) mounted to the support base (16);
a plate (70b) mounted to the at least one post (71a, 71b) at a fixed elevation above the support base (16) and having at least two threaded holes;
a slotted extension (100) which extends from a side of the tissue pusher (66) opposite the drum (20) and has two or more slots (101), each of which is sized and shaped to align with a corresponding one of the at least two threaded holes of the plate (70b); and
two or more knobs (106a, 106b) each having a threaded shaft sized and shaped to be threadedly received, through a respective one of the two or more slots (101), and in a respective one of the at least two threaded holes of the plate (70b),
whereby the tissue pusher (66) and slotted extension (100) are slidably movable together, in the same linear direction (TA) as, but independently of, the thickness adjustment mechanism (24), and secured in a fixed position by turning the two or more knobs (106a, 106b) until tight.

11. A device for producing a tissue product from a tissue sample, wherein the tissue product comprises a piece of tissue having a generally planar configuration and a predetermined maximum thickness between first and second surfaces thereof, the device comprising:

(A) a support base (16) for supporting the device on a horizontal surface;

(B) a drum assembly (12) mounted on the support base (16) and comprising:
a rotatable cylindrical drum (20) having a longitudinal axis (LA) oriented parallel to the horizontal surface and an exterior cylindrical surface (32),
a shaft (42) extending through the drum (20) coincident with the longitudinal axis (LA), and
a hand wheel mounted to the drum (20) capable of manually rotating the drum (20);

(C) a drum motor assembly (22) mounted to the support base (16) and operably engaged with the shaft (42) of the drum assembly (12) and capable of continuously rotating the drum (20) about the longitudinal axis (LA);

(D) a blade assembly (14) comprising a blade (64) which is longitudinally aligned with and proximate to the exterior surface (32) of the drum (20) and capable of cutting a tissue sample mounted on the exterior surface (32) to form the tissue product, the blade assembly (14) further comprising:
a holder (90) and a clamp (92) which securely hold the blade (64) therebetween; and
at least two shafts (98a, 98b) which are each affixed to (E) a lateral movement mechanism (30) and to either or both of the holder (90) and clamp (92), and which support the holder (90), blade (64) and clamp (92), which are assembled together, in an elevated position above the support base (16) and proximate to the exterior surface (32) of the drum (20);

(E) the lateral movement mechanism (30) operably engaged with and carrying the blade assembly (14) and capable of moving the blade assembly (14) reciprocatingly in a lateral direction (LM);

(F) a lateral drive assembly (28) operably engaged with and capable of operating the lateral movement mechanism (30) to move the blade assembly (14) reciprocatingly in a lateral direction (LM), wherein the lateral movement mechanism (30), the lateral drive assembly (28), and the blade assembly (14) are, together, capable of continuously cutting a tissue sample mounted on the exterior surface (32) of the drum (20) by reciprocatingly moving the blade assembly (14) and blade (64) thereof in the lateral direction (LM);

(G) a blade motor assembly (26) mounted to the support base (16) and operably engaged with and capable of actuating the lateral drive assembly (28) to operate the lateral movement mechanism (30); and (H) a thickness adjustment mechanism (24) which is partially mounted on the support base (16) and partially mounted to the lateral movement mechanism (30), thereby being operably engaged with the blade assembly (14), wherein the thickness adjustment mechanism (24) is capable of setting the maximum predetermined thickness of the tissue product by moving the blade assembly (14) in a linear direction (TA), which is perpendicular to the longitudinal axis (LA) of the drum (20), and positioning the blade (64) a distance (d) from the exterior surface (32) of the drum (20), wherein the distance (d) is equal to the maximum predetermined thickness of the tissue product.

12. A method for producing a tissue product from a tissue sample, wherein the tissue product comprises a piece of tissue having a generally planar configuration and a predetermined maximum thickness between first and second surfaces thereof, and wherein the method is performed using a device which comprises:

(A) a support base (16) for supporting the device on a horizontal surface;

(B) a drum assembly (12) mounted on the support base (16) and comprising:
a rotatable cylindrical drum (20) having a longitudinal axis (LA) oriented parallel to the horizontal surface and an exterior cylindrical surface (32),
a shaft (42) extending through the drum (20) coincident with the longitudinal axis (LA), and
a hand wheel mounted to the drum (20) capable of manually rotating the drum (20);

(C) a drum motor assembly (22) mounted to the support base (16) and operably engaged with the shaft (42) of the drum assembly (12) and capable of continuously rotating the drum (20) about the longitudinal axis (LA);

(D) a blade assembly (14) comprising a blade (64) which is longitudinally aligned with and proximate to the exterior surface (32) of the drum (20) and capable of cutting a tissue sample mounted on the exterior surface (32) to form the tissue product;

(E) a lateral movement mechanism (30) operably engaged with and carrying the blade assembly (14) and capable of moving the blade assembly (14) reciprocatingly in a lateral direction (LM);

(F) a lateral drive assembly (28) operably engaged with and capable of operating the lateral movement mechanism (30) to move the blade assembly (14) reciprocatingly in a lateral direction (LM), wherein the lateral movement mechanism (30), the lateral drive assembly (28), and the blade assembly (14) are, together, capable of continuously cutting a tissue sample mounted on the exterior surface (32) of the drum (20) by reciprocatingly moving the blade assembly (14) and blade (64) thereof in the lateral direction (LM);

(G) a blade motor assembly (26) mounted to the support base (16) and operably engaged with and capable of actuating the lateral drive assembly (28) to operate the lateral movement mechanism (30);

(H) a thickness adjustment mechanism (24) which is partially mounted on the support base (16) and partially mounted to the lateral movement mechanism (30), thereby being operably engaged with the blade assembly (14), wherein the thickness adjustment mechanism (24) is capable of setting the maximum predetermined thickness of the tissue product by moving the blade assembly (14) in a linear direction (TA), which is perpendicular to the longitudinal axis (LA) of the drum (20), and positioning the blade (64) a distance (d) from the exterior surface (32) of the drum (20), wherein the distance (d) is equal to the maximum predetermined thickness of the tissue product, the method comprising the sequential steps of:

(1) optionally, modifying the tissue sample to have a size and shape suitable for use with the device;

(2) mounting the tissue sample on the exterior surface of the drum (20);

(3) selecting and setting the maximum predetermined thickness of the tissue product by positioning the blade (64) of the blade assembly (14) a distance (d) from the exterior surface (32) of the drum (20), using the thickness adjustment mechanism (24);

(4) positioning the tissue sample in a suitable position relative to the blade (64) of the blade assembly (14) by manually rotating the drum (20) using the hand wheel, wherein the suitable position is when a leading edge of the tissue sample is proximate to but not yet in contact with the blade (64);

(5) commencing lateral reciprocating movement of the blade assembly (14) by supplying power to the blade motor assembly (26), which actuates the lateral drive assembly (28), which operates the lateral movement mechanism (30), which moves the blade assembly (14) reciprocatingly in the lateral direction (LM);

(6) commencing rotation of the drum (20) and the tissue sample mounted on the exterior surface (32) thereof by supplying power to the drum motor assembly (22);

(7) allowing the concurrent reciprocating movement of the blade assembly (14) and rotation of the drum (20) and the tissue sample mounted on the exterior surface (32) thereof to continue until all of the tissue sample has passed by the blade assembly (14) to form a first tissue product which remains on the drum (20) and a second piece of tissue which has been separated from the first tissue product;

(8) optionally, removing the first tissue product from the drum (20), wherein the first tissue product has a generally planar configuration, a predetermined maximum thickness, and, optionally, consists essentially of a selected tissue type;

(9) optionally, removing the first tissue product from the drum (20) and mounting the second piece of tissue to the exterior surface (32) of the drum (20) as a next tissue sample to be cut, and repeating steps (3) to (7); and

(10) optionally, leaving the first tissue product on the drum (20) and using the first tissue product as a next tissue sample to be cut, and repeating steps (4) to (7).

13. The method of claim 12, wherein the device further comprises (I) a tissue pusher assembly (15) comprising a tissue pusher (66) slidably mounted to the support base (16) and which is longitudinally aligned with and proximate to the exterior surface (32) of the drum (20), moveable in the same linear direction (TA) as, and independently of, the thickness adjustment mechanism (24), and capable of pressing and holding a tissue sample on the exterior surface (32) during operation of the device; and the method further comprises:

after the step of (2) mounting the tissue sample on the exterior surface (32) of the drum (20), and before the steps of (5) commencing lateral reciprocating movement of the blade assembly (14) and (6) commencing rotation of the drum (20) and the tissue sample mounted on the exterior surface (32) thereof, and positioning the tissue pusher (66) at a desired position and distance from the tissue sample whereby the tissue pusher (66) presses and holds the tissue sample on the exterior surface (32) of the drum (20).

14. The method of claim 12, wherein the tissue sample comprises dermal tissue.

15. A tissue product produced by the method of claim 12, wherein the tissue product has a generally planar configuration and a predetermined maximum thickness.

16. The tissue product of claim 15, wherein the tissue product comprises a selected tissue type.

17. The tissue product of claim 15, wherein the tissue product consists essentially of a selected tissue type.

18. The tissue product of claim 15, wherein the tissue sample comprises dermal tissue.

19. The tissue product of claim 18, wherein the tissue sample comprises processed dermal tissue, and wherein the tissue product consists essentially of reticular dermis and, optionally, at least a portion of papillary dermis.

* * * * *